United States Patent
Liao et al.

(10) Patent No.: US 11,731,934 B2
(45) Date of Patent: *Aug. 22, 2023

(54) HDAC INHIBITOR COMPOUNDS AND METHODS OF TREATMENT

(71) Applicants: University of Florida Research Foundation, Inc., Gainesville, FL (US); The Scripps Research Institute, La Jolla, CA (US)

(72) Inventors: Daiqing Liao, Gainesville, FL (US); William R. Roush, Jupiter, FL (US); Ryan L. Stowe, Jupiter, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 231 days.

This patent is subject to a terminal disclaimer.

(21) Appl. No.: 17/000,180

(22) Filed: Aug. 21, 2020

(65) Prior Publication Data

US 2021/0009509 A1  Jan. 14, 2021

Related U.S. Application Data

(63) Continuation of application No. 15/301,508, filed as application No. PCT/US2015/023437 on Mar. 30, 2015, now Pat. No. 10,807,944.

(60) Provisional application No. 62/117,326, filed on Feb. 17, 2015, provisional application No. 61/975,564, filed on Apr. 4, 2014.

(51) Int. Cl.

| | |
|---|---|
| C07C 233/77 | (2006.01) |
| A61K 31/166 | (2006.01) |
| C07C 243/38 | (2006.01) |
| A61K 45/06 | (2006.01) |
| C07C 247/12 | (2006.01) |
| C07D 239/26 | (2006.01) |
| C07D 213/86 | (2006.01) |
| A61K 31/4406 | (2006.01) |
| A61K 31/505 | (2006.01) |
| C07C 233/78 | (2006.01) |
| C07D 213/44 | (2006.01) |
| C07D 239/48 | (2006.01) |

(52) U.S. Cl.
CPC .......... *C07C 233/77* (2013.01); *A61K 31/166* (2013.01); *A61K 31/4406* (2013.01); *A61K 31/505* (2013.01); *A61K 45/06* (2013.01); *C07C 233/78* (2013.01); *C07C 243/38* (2013.01); *C07C 247/12* (2013.01); *C07D 213/44* (2013.01); *C07D 213/86* (2013.01); *C07D 239/26* (2013.01); *C07D 239/48* (2013.01); *C07C 2601/08* (2017.05)

(58) Field of Classification Search
None
See application file for complete search history.

(56) References Cited

U.S. PATENT DOCUMENTS

| | | | |
|---|---|---|---|
| 4,814,349 A | * | 3/1989 | Addor ................... A01N 37/40 564/150 |
| 7,981,874 B2 | | 7/2011 | Close et al. |
| 2007/0281934 A1 | | 12/2007 | Buggy et al. |
| 2009/0012075 A1 | | 1/2009 | Miller et al. |
| 2010/0247543 A1 | | 9/2010 | Maes et al. |
| 2012/0039909 A1 | | 2/2012 | Tsai et al. |
| 2013/0267542 A1 | | 10/2013 | Chern et al. |
| 2017/0174619 A1 | | 6/2017 | Liao et al. |

FOREIGN PATENT DOCUMENTS

| | | | |
|---|---|---|---|
| WO | WO 2008069619 | * | 6/2008 |
| WO | 2013025805 A1 | | 2/2013 |
| WO | 2021/119834 | | 6/2021 |

OTHER PUBLICATIONS

Li, et al. Class I HDAC Inhibitors Display Different Antitumor Mechanism in Leukemia and Prostatic Cancer Cells Depending on their p53 Status, J. Med. Chem., 61, 2589-2603, 2018.

McClure, et al. Development of Allosteric Hydrazide-Containing Class I Histone Deacetylase Inhibitors for Use in Acute Myeloid Leukemia, J. Med. Chem., 59, 9942-9959, 2016.

Mahmud, et al. Abstract LB248: Chemically distinct class I HDAC inhibitors to synergize to inhibit global lipid metabolism in cancer, Cancer Research, Molecular and Cellular Biology/Genetics, Jul. 2018.

International Search Report and Written Opinion dated Jul. 1, 2015 for PCT/US2015/023437.

Bertrand. Inside HDAC with HDAC inhibitors, Eur J Med Chem. Jun. 2020, 45(6): 2095-116.

Chen, et al. Discovery of structure-based small molecular inhibitor of alphaB-crystallin against basal-like/triple-negative breast cancer development in vitro and in vivo. Breast Cancer Res Treat. May 2014; 145(1): 45-59.

Kim, et al. Histone deacetylase inhibitors: molecular mechanisms of action and clinical trials as anti-cancer drugs Am J. Transl Res. Feb. 2011, 3(2): 166-79.

Wang, et al. Identification and characterization of class I HDAC-specific small molecule inhibitors with a novel pharmacore. Abstract presented at the American Association of Cancer Research (AACR) Conference. San Diego, CA. Apr. 7, 2014. Abstract #2525. 4 pages.

Wang, et al. Identification of histone deacetylase inhibitors with benzoylhydrazide scaffold that selectively inhibit class histone deacetylases, Chem Biol. Feb. 19, 2015; 22(2): 273-84.

(Continued)

*Primary Examiner* — Sudhakar Katakam
*Assistant Examiner* — Jennifer C Sawyer
(74) *Attorney, Agent, or Firm* — Thomas | Horstemeyer, LLP

(57) ABSTRACT

The instant invention describes hydrazide-containing compounds having therapeutic activity, and methods of treating disorders such as cancer, tumors and cell proliferation related disorders, or affect cell differentiation, dedifferentiation or transdifferentiation.

14 Claims, 13 Drawing Sheets

(56) References Cited

OTHER PUBLICATIONS

International Search Report for PCT/US22/73187 dated Oct. 28, 2022.
Colvin, E et al.) The Effects of Histone Deacetylase (HDAC) Inhibitors on FASN Intracellular Localization in Cancer Cells. Journal of Undergraduate Research, vol. 21, No. 2, 2020, p. 1-10; abstract; p. 7, figure 4.

* cited by examiner

HDAC INHIBITOR COMPOUNDS AND METHODS OF TREATMENT

CROSS REFERENCE TO RELATED APPLICATIONS

This application is a continuation of co-pending U.S. patent application Ser. No. 15/301,508, filed on Oct. 3, 2016, entitled "HDAC INHIBITOR COMPOUNDS AND METHODS OF TREATMENT," the contents of which are incorporated by reference herein in their entirety.

U.S. patent application Ser. No. 15/301,508 is the U.S. National Stage, pursuant to 35 U.S.C. 371, of International Application No. PCT/US2015/023437, filed Mar. 30, 2015, which claims the benefit of U.S. Provisional Patent Application Ser. No. 61/975,564, filed Apr. 4, 2014 and 62/117,326, filed Feb. 15, 2015, the contents of which are expressly incorporated by reference herein.

STATEMENT OF GOVERNMENT SUPPORT

This invention was made with government support under grant number MH84512 awarded by the National Institutes of Health. The government has certain rights to the invention.

BACKGROUND

Histone deacetylases (HDACs) remove the acetyl group from lysine residues of histones and other cellular proteins. HDACs are classified into four phylogenetic groups: class I (HDAC1, HDAC2, HDAC3 and HDAC8), class II (HDAC4, HDAC5, HDAC7 and HDAC9 in the class IIa subgroup, and HDAC6 and HDAC10 in the Ib subgroup), class III (Sirt1-Sirt7) and class IV (HDAC11) [Yang, X. J., and Seto, E. (2008). The Rpd3/Hda1 family of lysine deacetylases: from bacteria and yeast to mice and men. Nature reviews. Molecular cell biology 9, 206-218]. Classes I, Ib and IV HDACs possess bona fide $Zn^{2+}$-dependent acetyl-lysine deacetylase activities. While heightened HDAC activities have been implicated in several disorders including chronic neurologic, inflammatory and metabolic conditions [Christensen, D. P., Gysemans, C., Lundh, M., Dahllof, M. S., Noesgaard, D., Schmidt, S. F., Mandrup, S., Birkbak, N., Workman, C. T., Piemonti, L., et al. (2014). Lysine deacetylase inhibition prevents diabetes by chromatin-independent immunoregulation and beta-cell protection. Proceedings of the National Academy of Sciences of the United States of America 111, 1055-1059], abnormal epigenetic regulation, including globally or locally altered patterns of histone acetylation, has long been implicated in cancer etiology and progression. In particular, the roles of HDAC1, HDAC2 and HDAC3 in promoting cancer progression have been extensively documented [Muller, B. M., Jana, L., Kasajima, A., Lehmann, A., Prinzler, J., Budczies, J., Winzer, K. J., Dietel, M., Weichert, W., and Denkert, C. (2013). Differential expression of histone deacetylases HDAC1, 2 and 3 in human breast cancer—overexpression of HDAC2 and HDAC3 is associated with clinicopathological indicators of disease progression. BMC cancer 13, 215; New, M., Olzscha, H., and La Thangue, N. B. (2012). HDAC inhibitor-based therapies: can we interpret the code? Molecular oncology 6, 637-656; Wilson, A. J., Byun, D. S., Popova, N., Murray, L. B., L'Italien, K., Sowa, Y., Arango, D., Velcich, A., Augenlicht, L. H., and Mariadason, J. M. (2006). Histone deacetylase 3 (HDAC3) and other class I HDACs regulate colon cell maturation and p21 expression and are deregulated in human colon cancer. The Journal of biological chemistry 281, 13548-13558].

Chemically diverse classes of small-molecule inhibitors of HDACs (HDACi) have been developed and characterized, and many exhibit potent anticancer properties in preclinical and clinical studies [Bolden, J. E., Peart, M. J., and Johnstone, R. W. (2006). Anticancer activities of histone deacetylase inhibitors. Nature reviews. Drug discovery 5, 769-784; Bradner, J. E., West, N., Grachan, M. L., Greenberg, E. F., Haggarty, S. J., Warnow, T., and Mazitschek, R. (2010). Chemical phylogenetics of histone deacetylases. Nature chemical biology 6, 238-243]. Based on the structures of the $Zn^{2+}$-chelating chemical groups contained in these inhibitors, known HDAC inhibitors can be divided into four major classes: hydroxamic acids, aminobenzamides, cyclic peptides and aliphatic acids. A variety of derivatives of each class have been synthesized and characterized. Two compounds, vorinostat (a hydroxamic acid) and romidepsin (a cyclic peptide), have been approved for clinical anticancer therapies [Marks, P. A. (2010). The clinical development of histone deacetylase inhibitors as targeted anticancer drugs. Expert opinion on investigational drugs 19, 1049-1066; New, M., Olzscha, H., and La Thangue, N. B. (2012). HDAC inhibitor-based therapies: can we interpret the code? Molecular oncology 6, 637-656]. These FDA approved drugs and a number of other HDACi have been undergoing clinical evaluations for treating a variety of hematological malignancies and solid tumors [New, M., Olzscha, H., and La Thangue, N. B. (2012). HDAC inhibitor-based therapies: can we interpret the code? Molecular oncology 6, 637-656].

However, there are a number of issues that may limit broad clinical utility of the currently known classes of HDACi. Hydroxamic acids are pan-HDACi, active against different isoforms of HDACs and feature a rather strong $Zn^{2+}$-chelating group (warhead) that are also found in inhibitors of other metalloenzymes such as matrix metalloproteases and TNF-α-converting enzyme [DasGupta, S., Murumkar, P. R., Giridhar, R., and Yadav, M. R. (2009). Current perspective of TACE inhibitors: a review. Bioorganic & medicinal chemistry 17, 444-459; Lotsch, J., Schneider, G., Reker, D., Parnham, M. J., Schneider, P., Geisslinger, G., and Doehring, A. (2013). Common non-epigenetic drugs as epigenetic modulators. Trends in molecular medicine 19, 742-753; Nuti, E., Casalini, F., Santamaria, S., Gabelloni, P., Bendinelli, S., Da Pozzo, E., Costa, B., Marinelli, L., La Pietra, V., Novellino, E., et al. (2011). Synthesis and biological evaluation in U87MG glioma cells of (ethynylthiophene)sulfonamido-based hydroxamates as matrix metalloproteinase inhibitors. European journal of medicinal chemistry 46, 2617-2629], raising the risks of significant off-target activities and unpredictable clinical toxicity. Although several mechanisms such as the induction of apoptosis, cell cycle arrest or inhibition of DNA repair have been proposed to account for antineoplastic activities of HDACi, it remains challenging to determine precisely the importance of HDAC inhibition for anticancer effects using pan-HDACi due to off-target activities. Although yet to be proven, it is generally thought that HDACi with increased isoform-selectivity and potency would be safer agents with reduced side effects and could lead to superior clinical outcomes, because such selective compounds would only target HDAC activities that are dysregulated in a particular type of cancer without causing unnecessary toxicity stemming from inhibiting other HDAC isoforms. Thus, there have been significant efforts in drug development to identify HDACi with greater isozyme-specificity [Ononye, S. N., van Heyst, M., Falcone, E. M., Anderson, A. C., and Wright, D. L. (2012). Toward isozyme-selective inhibitors of histone deacetylase as therapeutic agents for the treatment of cancer. Pharmaceutical patent analyst 1, 207-221]. The aminobenzamide class of HDACi are selective to class I HDACs (HDAC1-3) and display a unique slow-on/slow-off HDAC-binding kinetics [Beconi, M., Aziz, O., Matthews, K., Moumne, L., O'Connell, C., Yates, D., Clifton, S., Pett, H., Vann, J., Crowley, L., et al. (2012). Oral administration of the pimelic diphenylamide HDAC inhibitor HDACi 4b is unsuitable for chronic inhibition of HDAC activity in the CNS in vivo. PloS one 7, e44498; Chou, C. J., Herman, D., and Gottesfeld, J. M. (2008). Pimelic diphenylamide 106 is a slow, tight-binding inhibitor of class I histone deacetylases. The Journal of biological chemistry 283, 35402-35409; Lauffer, B. E., Mintzer, R., Fong, R., Mukund, S., Tam, C., Zilberleyb, I., Flicke, B., Ritscher, A., Fedorowicz, G., Vallero, R., et al. (2013). Histone deacetylase (HDAC) inhibitor kinetic rate constants correlate with cellular histone acetylation but not transcription and cell viability. The Journal of biological chemistry 288, 26926-26943; Newbold, A., Matthews, G. M., Bots, M., Cluse, L. A., Clarke, C. J., Banks, K. M., Cullinane, C., Bolden, J. E., Christiansen, A. J., Dickins, R. A., et al. (2013). Molecular and biologic analysis of histone deacetylase inhibitors with diverse specificities. Molecular cancer therapeutics 12, 2709-2721] and a number of these compounds such as MS-275 (entinostat) have been tested in clinical trials to treat diverse types of human cancer [Gojo, I., Jiemjit, A., Trepel, J. B., Sparreboom, A., Figg, W. D., Rollins, S., Tidwell, M. L., Greer, J., Chung, E. J., Lee, M. J., et al. (2007). Phase 1 and pharmacologic study of MS-275, a histone deacetylase inhibitor, in adults with refractory and relapsed acute leukemias. Blood 109, 2781-2790; Martinet, N., and Bertrand, P. (2011). Interpreting clinical assays for histone deacetylase inhibitors. Cancer management and research 3, 117-141]. However, aminobenzamides exhibit intrinsic liabilities including chemical instability under certain conditions, high in vivo metabolic turnover, and efficient removal by Pgp drug transporter, which could significantly hamper their potential clinical utility [Beconi, M., Aziz, O., Matthews, K., Moumne, L., O'Connell, C., Yates, D., Clifton, S., Pett, H., Vann, J., Crowley, L., et al. (2012). Oral administration of the pimelic diphenylamide HDAC inhibitor HDACi 4b is unsuitable for chronic inhibition of HDAC activity in the CNS in vivo. PloS one 7, e44498]. Although cyclic peptides are more potent against the class I HDACs [Bradner, J. E., West, N., Grachan, M. L., Greenberg, E. F., Haggarty, S. J., Warnow, T., and Mazitschek, R. (2010). Chemical phylogenetics of histone deacetylases. Nature chemical biology 6, 238-243], the sulfhydryl group of romidepsin is thought to chelate zinc with little specificity [Arrowsmith, C. H., Bountra, C., Fish, P. V., Lee, K., and Schapira, M. (2012). Epigenetic protein families: a new frontier for drug discovery. Nature reviews. Drug discovery 11, 384-400]. Moreover, serious adverse events associated with cyclic peptides including cardiac toxicity have been reported [Martinet, N., and Bertrand, P. (2011). Interpreting clinical assays for histone deacetylase inhibitors. Cancer management and research 3, 117-141]. These observations call for potent and isoform-selective HDACi of novel chemotypes to overcome these limitations and to unleash the considerable therapeutic potentials of pharmacological HDAC inhibition.

BRIEF SUMMARY OF THE INVENTION

The invention is directed towards hydrazide-containing compounds, and methods of treating disease and disorders, including proliferation diseases and disorders, and HDAC mediated diseases and disorders, by use of the compounds and compositions thereof.

The invention is directed towards hydrazide-containing compounds, methods of modulating proliferation activity, and methods of treating proliferation disease and disorders.

In one embodiment, the invention provides a compound according to Formula I:

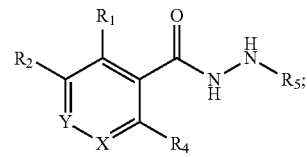

wherein:

X is N or CH;

Y is N or C—$R_3$;

$R_1$ is H, halo, optionally substituted aryl, optionally substituted alkyl, haloalkyl, alkoxy, nitro, haloalkoxy,

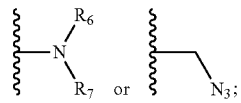

$R_2$ is H, halo, optionally substituted aryl, optionally substituted alkyl, haloalkyl, alkoxy, nitro, haloalkoxy,

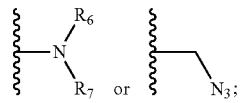

$R_3$ is halo, optionally substituted aryl, optionally substituted alkyl, haloalkyl, alkoxy, nitro, haloalkoxy,

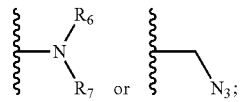

or $R_2$ and $R_3$ taken together with the carbon atoms to which they are attached form an aryl ring;

$R_4$ is H or OH;

$R_5$ is H or alkyl optionally substituted with cycloalkyl; and $R_6$ and $R_7$ are each independently H or optionally substituted alkyl;

provided that if $R_3$ is halo, then $R_5$ is $C_{1-3}$ alkyl, $C_{5-12}$ alkyl, or $C_{1-12}$ alkyl substituted with cycloalkyl;

and pharmaceutically acceptable salts, solvates, or hydrates thereof.

In another aspect, the invention provides a compound according to Formula I:

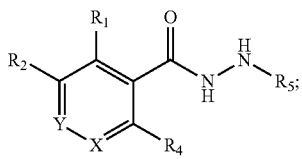

wherein:
X is N or CH;
Y is N or C—R₃;
R₁ is H, halo, optionally substituted aryl, optionally substituted alkyl, haloalkyl, alkoxy, nitro, haloalkoxy,

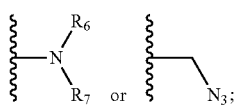

R₂ is H, halo, optionally substituted aryl, optionally substituted alkyl, haloalkyl, alkoxy, nitro, haloalkoxy,

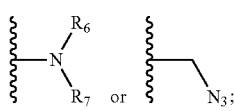

R₃ is halo, optionally substituted aryl, optionally substituted alkyl, haloalkyl, alkoxy, nitro, haloalkoxy,

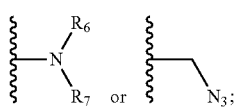

or R₂ and R₃ taken together with the carbon atoms to which they are attached form an aryl ring;
R₄ is H or OH;
R₅ is H or alkyl optionally substituted with cycloalkyl; and
R₆ and R₇ are each independently H or optionally substituted alkyl;
provided that when Y is C—R₃, R₁ is H, R₂ is H, R₃ is halo, R₄ is H, and X is CH, then R₅ is $C_{1-3}$ alkyl, $C_{5-12}$ alkyl, or $C_{1-12}$ alkyl substituted with cycloalkyl;
and pharmaceutically acceptable salts, solvates, or hydrates thereof.

In another aspect, the invention provides a compound according to Formula I:

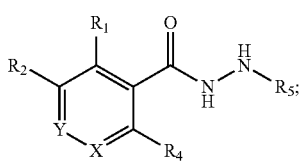

wherein:
X is N or CH;
Y is N or C—R₃;
R₁ is H, halo, optionally substituted aryl, optionally substituted alkyl, haloalkyl, alkoxy, nitro, haloalkoxy,

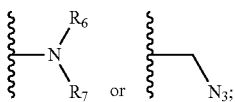

R₂ is H, halo, optionally substituted aryl, optionally substituted alkyl, haloalkyl, alkoxy, nitro, haloalkoxy,

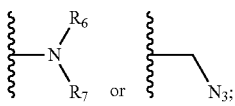

R₃ is optionally substituted aryl, optionally substituted alkyl, haloalkyl, alkoxy, nitro, haloalkoxy,

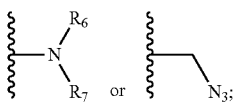

or N₃; or R₂ and R₃ taken together with the carbon atoms to which they are attached form an aryl ring;
R₄ is H or OH;
R₅ is H or alkyl optionally substituted with cycloalkyl; and
R₆ and R₇ are each independently H or optionally substituted alkyl;
and pharmaceutically acceptable salts, solvates, or hydrates thereof.

In one embodiment, the invention provides a compound according to Formula I:

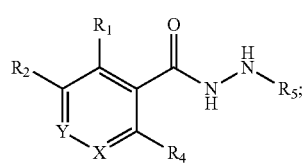

wherein:
X is N or CH;
Y is N or C—R₃;
R₁ is H, halo, optionally substituted aryl, optionally substituted alkyl, haloalkyl, alkoxy, nitro, haloalkoxy,

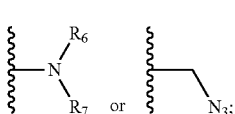

R₂ is H, halo, optionally substituted aryl, optionally substituted alkyl, haloalkyl, alkoxy, nitro, haloalkoxy,

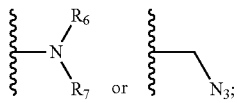 or 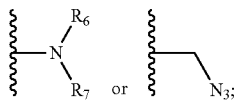

or $R_2$ and $R_3$ taken together with the carbon atoms to which they are attached form an aryl ring;

$R_4$ is H or OH;

$R_5$ is H or alkyl optionally substituted with cycloalkyl; and $R_6$ and $R_7$ are each independently H or optionally substituted alkyl;

provided that if $R_3$ is halo, then $R_5$ is $C_{1-3}$ alkyl, $C_{5-12}$ alkyl, or $C_{1-12}$ alkyl substituted with cycloalkyl;

and pharmaceutically acceptable salts, solvates, or hydrates thereof.

In another aspect, the invention provides a compound according to Formula I:

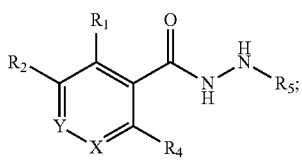

I wherein:

X is N or CH;

Y is N or C—$R_3$;

$R_1$ is H, halo, optionally substituted aryl, optionally substituted alkyl, haloalkyl, alkoxy, nitro, haloalkoxy,

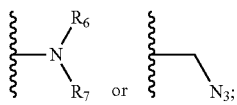 or 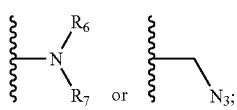

$R_2$ is H, halo, optionally substituted aryl, optionally substituted alkyl, haloalkyl, alkoxy, nitro, haloalkoxy,

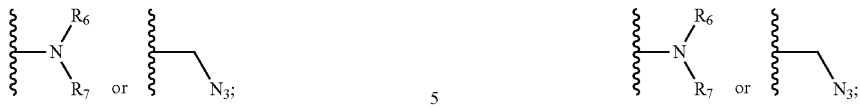

$R_3$ is halo, optionally substituted aryl, optionally substituted heteroaryl, optionally substituted alkyl, haloalkyl, alkoxy, nitro, haloalkoxy,

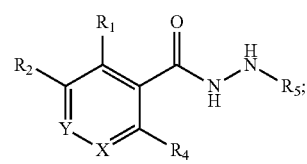

or $R_2$ and $R_3$ taken together with the carbon atoms to which they are attached form an aryl ring;

$R_4$ is H or OH;

$R_5$ is H or alkyl optionally substituted with cycloalkyl; and $R_6$ and $R_7$ are each independently H or optionally substituted alkyl;

provided that when Y is C—$R_3$, $R_1$ is H, $R_2$ is H, $R_3$ is halo, $R_4$ is H, and X is CH, then $R_5$ is $C_{1-3}$ alkyl, $C_{5-12}$ alkyl, or $C_{1-12}$ alkyl substituted with cycloalkyl.

and pharmaceutically acceptable salts, solvates, or hydrates thereof.

In another aspect, the invention provides a compound according to Formula I:

I wherein:

X is N or CH;

Y is N or C—$R_3$;

$R_1$ is H, halo, optionally substituted aryl, optionally substituted alkyl, haloalkyl, alkoxy, nitro, haloalkoxy,

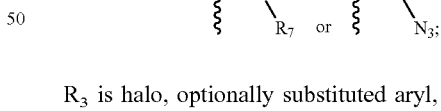

$R_2$ is H, halo, optionally substituted aryl, optionally substituted alkyl, haloalkyl, alkoxy, nitro, haloalkoxy

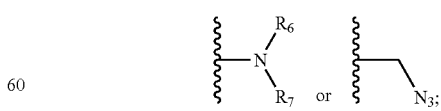

$R_3$ is halo, optionally substituted aryl, optionally substituted heteroaryl, optionally substituted alkyl, haloalkyl, alkoxy, nitro, haloalkoxy, or $R_2$ and $R_3$ taken together with the carbon atoms to which they are attached form an aryl ring;

$R_4$ is H or OH;

$R_5$ is H or alkyl optionally substituted with cycloalkyl; and $R_6$ and $R_7$ are each independently H or optionally substituted alkyl;

and pharmaceutically acceptable salts, solvates, or hydrates thereof.

In another aspect, the invention provides a compound according to Formula I:

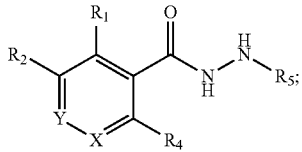

I wherein:
X is N or CH;
Y is N or C—$R_3$;
$R_1$ is H, halo, optionally substituted aryl, optionally substituted alkyl, haloalkyl, alkoxy, nitro, haloalkoxy,

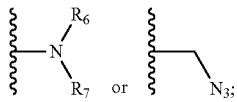

$R_2$ is H, halo, optionally substituted aryl, optionally substituted alkyl, haloalkyl, alkoxy, nitro, haloalkoxy,

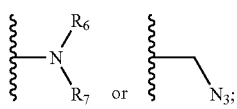

$R_3$ is halo;
$R_4$ is H or OH;
$R_5$ is $C_{1-3}$ alkyl, $C_{5-12}$ alkyl, or $C_{1-12}$ alkyl substituted with cycloalkyl; and
$R_6$ and $R_7$ are each independently H or optionally substituted alkyl;

and pharmaceutically acceptable salts, solvates, or hydrates thereof.

Another aspect is a compound of the formulae herein, wherein $R_1$ and $R_4$ are H.

Another aspect is a compound of the formulae herein, wherein $R_1$ and $R_4$ are H;
and $R_5$ is $C_1$-$C_6$ alkyl or (cycloalkyl)alkyl.

Another aspect is a compound of the formulae herein, wherein $R_1$ and $R_4$ are H;
and $R_5$ is n-Pr, n-Bu, n-pentyl, n-hexyl,

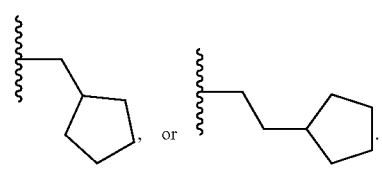 [SMILES: *CC1CCCC1 ; *CCC1CCCC1]

Another aspect is a compound of the formulae herein, wherein $R_1$ and $R_4$ are H;
and $R_5$ is n-Pr, n-Bu, Br, n-pentyl, n-hexyl,

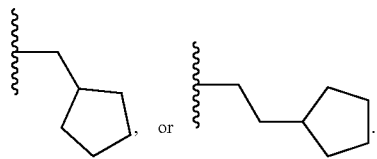 [SMILES: *CC1CCCC1 ; *CCC1CCCC1]

Another aspect is a compound of the formulae herein, wherein $R_1$, $R_2$, and $R_4$ are H; and $R_5$ is n-Bu,

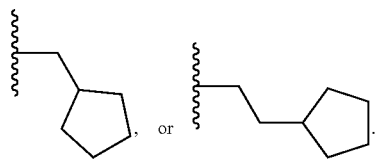 [SMILES: *CC1CCCC1 ; *CCC1CCCC1]

Another aspect is a compound of the formulae herein, wherein $R_1$, $R_2$, and $R_4$ are H; $R_5$ is n-Bu,

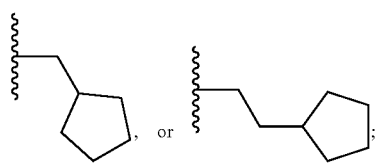 [SMILES: *CC1CCCC1 ; *CCC1CCCC1]

Y is C—$R_3$; and $R_3$ is NMe$_2$, halo, alkyl, aryl, or

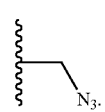

In another aspect, $R_3$ is NMe$_2$, Br, t-Bu, phenyl, or

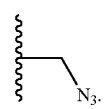

Another aspect is a compound of the formulae herein, wherein $R_1$, $R_2$, and $R_4$ are H; $R_5$ is n-Bu,

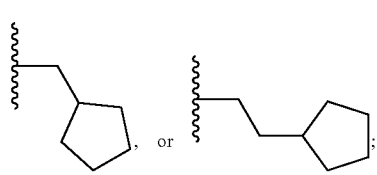 [SMILES: *CC1CCCC1 ; *CCC1CCCC1]

Y is C—$R_3$; and $R_3$ is NMe$_2$, alkyl, aryl, or

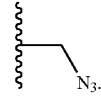

In another aspect, $R_3$ is $NMe_2$, t-Bu, phenyl, or

Another aspect is a compound of the formulae herein, wherein $R_1$ and $R_4$ are H; $R_2$ is alkoxy; and $R_5$ is $C_1$-$C_6$ alkyl or (cycloalkyl)alkyl.

Another aspect is a compound of the formulae herein, wherein $R_1$ and $R_4$ are H; $R_2$ and $R_3$ are alkoxy; and $R_5$ is $C_1$-$C_6$ alkyl or (cycloalkyl)alkyl. In another aspect, $R_2$ and $R_3$ are ethoxy.

Another aspect is a compound of formula II:

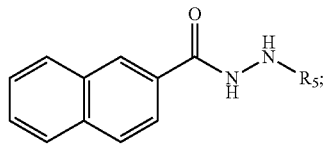

II wherein $R_5$ is $C_1$-$C_6$ alkyl or (cycloalkyl)alkyl;
and pharmaceutically acceptable salts, solvates, or hydrates thereof. In another aspect, $R_5$ is n-Pr or n-Bu.

Another aspect is a compound selected from the group consisting of:
N'-butyl-4-(trifluoromethoxy)benzohydrazide (RLS2-124);
N'-butyl-4-methoxybenzohydrazide (RLS2-126);
N'-butyl-4-nitrobenzohydrazide (RLS2-128);
N'-butyl-4-(dimethylamino)benzohydrazide (RLS2-131);
4-bromo-N'-propylbenzohydrazide (RLS2-137);
N'-tert-butyl-4-methylbenzohydrazide (RLS2-187);
N'-butyl-3-hydroxy-2-naphthohydrazide (RLS2-210);
4-bromo-N'-(2-cyclopentylethyl)benzohydrazide (RLS2-219);
N'-(cyclopentylmethyl)-4-(dimethylamino)benzohydrazide (RLS2-225);
N'-butyl-2-naphthohydrazide (RLS2-238);
N'-ethyl-2-naphthohydrazide (RLS2-240);
4-tert-butyl-N'-butylbenzohydrazide (RLS2-211);
N'-(2-cyclopentylethyl)-2-naphthohydrazide (RLS2-249);
N'-(cyclopentylmethyl)-2-naphthohydrazide (RLS2-254);
N'-propyl-2-naphthohydrazide (RLS2-255);
4-bromo-N'-(cyclopentylmethyl)benzohydrazide (RLS2-256);
4-bromo-N'-(2-cyclopentylethyl)benzohydrazide (RLS2-257);
4-tert-butyl-N'-hexylbenzohydrazide (RLS2-283);
4-bromo-N'-hexylbenzohydrazide (RLS2-284);
N'-butylnicotinohydrazide (RLS2-289);
N'-butylisonicotinohydrazide (RLS2-290);
N'-butyl-3-ethoxybenzohydrazide (RLS2-303);
N'-butyl-2-fluorobenzohydrazide (RLS2-305);
N'-butyl-3-fluorobenzohydrazide (RLS2-306);
4-(azidomethyl)-N'-butylbenzohydrazide (RLS2-312);
N'-butylbiphenyl-2-carbohydrazide (RLS3-4);
N'-butyl-3-iodobenzohydrazide (RLS3-5);
N'-butyl-3-(trifluoromethyl)benzohydrazide (RLS3-6);
3,4-dimethoxy-N'-pentylbenzohydrazide (RLS3-11);
3,4-diethoxy-N'-pentylbenzohydrazide (RLS3-14);
N'-pentylbiphenyl-4-carbohydrazide (RLS3-43);
N'-butyl-4-(pyrimidin-5-yl)benzohydrazide (SR-4369);
N'-butyl-2',3'-difluorobiphenyl-4-carbohydrazide (SR-4370);
N'-butyl-3'-fluoro-5'-methylbiphenyl-4-carbohydrazide (SR-4372); and
ethyl 4'-(2-butylhydrazinecarbonyl)-6-fluorobiphenyl-3-carboxy late (SR-4373).

In other aspects, the invention provides a method of treating a disease, disorder, or symptom thereof in a subject, comprising administering to the subject a compound of any of the formulae herein (e.g., formula I, formula II). In another aspect, the compound is administered in an amount and under conditions sufficient to ameliorate the disease, disorder, or symptom thereof in a subject. In another aspect, the disease or disorder is proliferative diseases, cancer, diabetes, cardiac hypertrophy, neurologic disorders, and/or psychiatric disorders. [Christensen, D. P., Gysemans, C., Lundh, M., Dahllof, M. S., Noesgaard, D., Schmidt, S. F., Mandrup, S., Birkbak, N., Workman, C. T., Piemonti, L., et al. (2014). Lysine deacetylase inhibition prevents diabetes by chromatin-independent immunoregulation and beta-cell protection. Proceedings of the National Academy of Sciences of the United States of America 111, 1055-1059; Ferguson B S et al., 2013; Schroeder, F. A., Lewis, M. C., Fass, D. M., Wagner, F. F., Zhang, Y L., Hennig, K. M., Gale, J., Zhao, W. N., Reis, S., Barker, D. D., et al. (2013). A selective HDAC 1/2 inhibitor modulates chromatin and gene expression in brain and alters mouse behavior in two mood-related tests. PloS one 8, e71323]

In other aspects, the invention provides a method of modulating HDAC activity in a subject, comprising contacting the subject with a compound of any of the formulae herein (e.g., formula I or formula II), in an amount and under conditions sufficient to modulate HDAC activity. In another aspect, the modulation is inhibition.

In other aspects, the invention provides a method of modulating the proliferation activity in a subject, comprising contacting the subject with a compound of any of the formulae herein (e.g., formula I or formula II), in an amount and under conditions sufficient to modulate proliferation activity.

In other aspects, the invention provides a method of modulating the activity of cell proliferation in a subject, comprising contacting the subject with a compound of any of the formulae herein (e.g., formula I or formula II), in an amount and under conditions sufficient to modulate cell proliferation activity. In another aspect, the cell is a cancer cell. In another aspect, the cell is a tumor cell. In another aspect, the modulation is inhibition.

In one aspect, the invention provides a method of treating a subject suffering from or susceptible to a proliferation related disorder or disease, comprising administering to the subject an effective amount of a compound or pharmaceutical composition of any of the formulae herein (e.g., formula I or formula II).

In another aspect, the invention provides a method of treating a subject suffering from or susceptible to a proliferation related activity related disorder or disease, wherein the subject has been identified as in need of treatment for a proliferation related disorder or disease, comprising administering to said subject in need thereof, an effective amount of a compound or pharmaceutical composition of any of the formulae herein (e.g., formula I or formula II), such that said subject is treated for said disorder.

In another aspect, the invention provides a method of treating a subject suffering from or susceptible to a cell proliferation related disorder or disease, wherein the subject has been identified as in need of treatment for a cell proliferation related disorder or disease, comprising administering to said subject in need thereof, an effective amount of a compound or pharmaceutical composition of any of the formulae herein (e.g., formula I or formula II), such that cell proliferation in said subject is modulated (e.g., down regulated). In another aspect, the compounds delineated herein preferentially target cancer cells over nontransformed cells.

In a specific aspect, the invention provides a method of treating cancer, tumor growth, cancer of the colon, breast, bone, brain and others (e.g., osteosarcoma, neuroblastoma, colon adenocarcinoma), comprising administering to said subject in need thereof, an effective amount of a compound delineated herein (e.g., Formula I or Formula II), and pharmaceutically acceptable salts thereof. Other cancers that may be treated by the compositions and methods of the invention include cardiac cancer (e.g., sarcoma, myxoma, rhabdomyoma, fibroma, lipoma and teratoma); lung cancer (e.g., bronchogenic carcinoma, alveolar carcinoma, bronchial adenoma, sarcoma, lymphoma, chondromatous hamartoma, mesothelioma); various gastrointestinal cancer (e.g., cancers of esophagus, stomach, pancreas, small bowel, and large bowel); genitourinary tract cancer (e.g., kidney, bladder and urethra, prostate, testis; liver cancer (e.g., hepatoma, cholangiocarcinoma, hepatoblastoma, angiosarcoma, hepatocellular adenoma, hemangioma); bone cancer (e.g., osteogenic sarcoma, fibrosarcoma, malignant fibrous histiocytoma, chondrosarcoma, Ewing's sarcoma, malignant lymphoma, cutaneous T-cell lymphoma, multiple myeloma, malignant giant cell tumor chordoma, osteochronfroma, benign chondroma, chondroblastoma, chondromyxofibroma, osteoid osteoma and giant cell tumors); cancers of the nervous system (e.g., of the skull, meninges, brain, and spinal cord); gynecological cancers (e.g., uterus, cervix, ovaries, vulva, vagina); hematologic cancer (e.g., cancers relating to blood, Hodgkin's disease, non-Hodgkin's lymphoma); skin cancer (e.g., malignant melanoma, basal cell carcinoma, squamous cell carcinoma, Karposi's sarcoma, moles dysplastic nevi, lipoma, angioma, dermatofibroma, keloids, psoriasis); and cancers of the adrenal glands (e.g., neuroblastoma). Other diseases and disorders that can be treated include the treatment of inflammatory disorders, neurodegenerative diseases, protozoal and latent viral infections, and (fibro)proliferative disorders.

In another aspect, the invention provides a method of inhibiting histone deacetylase (HDAC) in a subject in need thereof comprising administering to said subject, an effective amount of a compound delineated herein (e.g., Formula I or Formula II), and pharmaceutically acceptable salts thereof.

In another aspect, the invention provides a method of treating diseases, disorders, or symptoms thereof mediated by inhibition of histone deacetylase (HDAC) in a subject in need thereof comprising administering to said subject, an effective amount of a compound delineated herein (e.g., Formula I or Formula II), and pharmaceutically acceptable salts thereof. In another aspect, the HDAC-mediated disease or disorder is proliferative diseases, cancer, diabetes, cardiac hypertrophy, neurologic disorders, and/or psychiatric disorders. [Christensen, D. P., Gysemans, C., Lundh, M., Dahllof, M. S., Noesgaard, D., Schmidt, S. F., Mandrup, S., Birkbak, N., Workman, C. T., Piemonti, L., et al. (2014). Lysine deacetylase inhibition prevents diabetes by chromatin-independent immunoregulation and beta-cell protection. Proceedings of the National Academy of Sciences of the United States of America 111, 1055-1059; Ferguson B S et al., 2013; Schroeder, F. A., Lewis, M. C., Fass, D. M., Wagner, F. F., Zhang, Y L., Hennig, K. M., Gale, J., Zhao, W. N., Reis, S., Barker, D. D., et al. (2013). A selective HDAC 1/2 inhibitor modulates chromatin and gene expression in brain and alters mouse behavior in two mood-related tests. PloS one 8, e71323]

In another aspect, the compounds of any of the formulae herein (e.g., formula I or formula II) are compounds having class I HDAC selectivity, thus they are useful as anticancer agents; and furthermore having selectivity for class I HDAC versus class II HDAC also provides a more desirable therapeutic profile as it is indicated that inhibition of certain specific class II HDACs may have undesirable consequences, including for example, promoting cardiac hypertrophy. See, Furumai et al. Cancer Research 2002, 62, 4916-4921; Yurek-George et al. J. Med. Chem. 2007, 50, 5720-5726. Thus, in one aspect, the compounds and methods herein are those wherein the compounds demonstrate selectivity in class I/class II HDAC selectivity (e.g., at least 2-fold, at least 10-fold, at least 100-fold, at least 1000-fold, at least X-fold where X is any number between 1 and 100,000 inclusive).

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

In any of the methods delineated herein, the compound of Formula I or Formula II may be selected from the group consisting of:

4-bromo-N'-butylbenzohydrazide (RLS2-134, also known as UF010);
4-fluoro-N'-butylbenzohydrazide (RLS2-123);
N'-butyl-4-(trifluoromethoxy)benzohydrazide (RLS2-124);
N'-butyl-4-methylbenzohydrazide (RLS2-125);
N'-butyl-4-methoxybenzohydrazide (RLS2-126);
N'-butyl-4-nitrobenzohydrazide (RLS2-128);
N'-butyl-4-(dimethylamino)benzohydrazide (RLS2-131);
4-chloro-N'-butylbenzohydrazide (RLS2-133);
4-bromo-N'-propylbenzohydrazide (RLS2-137);
4-bromo-N'-phenethylbenzohydrazide (RLS2-138);
N'-isopropylbenzohydrazide (RLS2-185);
N'-tert-butyl-4-methylbenzohydrazide (RLS2-187);
N'-butyl-3-hydroxy-2-naphthohydrazide (RLS2-210);
4-bromo-N'-(2-cyclopentylethyl)benzohydrazide (RLS2-219);
N'-(cyclopentylmethyl)-4-(dimethylamino)benzohydrazide (RLS2-225);
N'-butyl-2-naphthohydrazide (RLS2-238);
N'-ethyl-2-naphthohydrazide (RLS2-240);
2-naphthohydrazide (RLS2-243);
4-tert-butyl-N'-butylbenzohydrazide (RLS2-211);
N'-(2-cyclopentylethyl)-2-naphthohydrazide (RLS2-249);
N'-(cyclopentylmethyl)-2-naphthohydrazide (RLS2-254);
N'-propyl-2-naphthohydrazide (RLS2-255);
4-bromo-N'-(cyclopentylmethyl)benzohydrazide (RLS2-256);
4-bromo-N'-(2-cyclopentylethyl)benzohydrazide (RLS2-257);
4-tert-butyl-N'-hexylbenzohydrazide (RLS2-283);
4-bromo-N'-hexylbenzohydrazide (RLS2-284);
N'-butylnicotinohydrazide (RLS2-289);
N'-butylisonicotinohydrazide (RLS2-290);
N'-butyl-3-ethoxybenzohydrazide (RLS2-303);
N'-butyl-2-fluorobenzohydrazide (RLS2-305);
N'-butyl-3-fluorobenzohydrazide (RLS2-306);
4-(azidomethyl)-N'-butylbenzohydrazide (RLS2-312);
N'-butylbiphenyl-2-carbohydrazide (RLS3-4);

N'-butyl-3-iodobenzohydrazide (RLS3-5);
N'-butyl-3-(trifluoromethyl)benzohydrazide (RLS3-6);
3,4-dimethoxy-N'-pentylbenzohydrazide (RLS3-11);
3,4-diethoxy-N'-pentylbenzohydrazide (RLS3-14);
N'-pentylbiphenyl-4-carbohydrazide (RLS3-43).
N'-butyl-4-(pyrimidin-5-yl)benzohydrazide (SR-4369);
N'-butyl-2',3'-difluorobiphenyl-4-carbohydrazide (SR-4370);
N'-butyl-3'-fluoro-5'-methylbiphenyl-4-carbohydrazide (SR-4372); and
ethyl 4'-(2-butylhydrazinecarbonyl)-6-fluorobiphenyl-3-carboxylate (SR-4373).

BRIEF DESCRIPTION OF THE DRAWINGS

The present invention is further described below with reference to the following non-limiting examples and with reference to the following figures, in which:

FIG. 1 (B) depicts the levels of acetylated histones at various histone sites (e.g., H4K5ac and H3K18ac) in HCT116 cells upon exposure to Trichostatin A (TSA, 0.1 µM), Romidepsin (5 nM), and 0.5 µM of UF010, RLS2-125, RLS2-131, RLS2-133, RLS2-137, RLS2-211, MS-275, and Vorinostat for 24 h. The total cell extracts were subject to WB with antibodies to histones with the indicated modifications. PCNA was detected as a loading control.

DETAILED DESCRIPTION

Definitions

Figure 1:
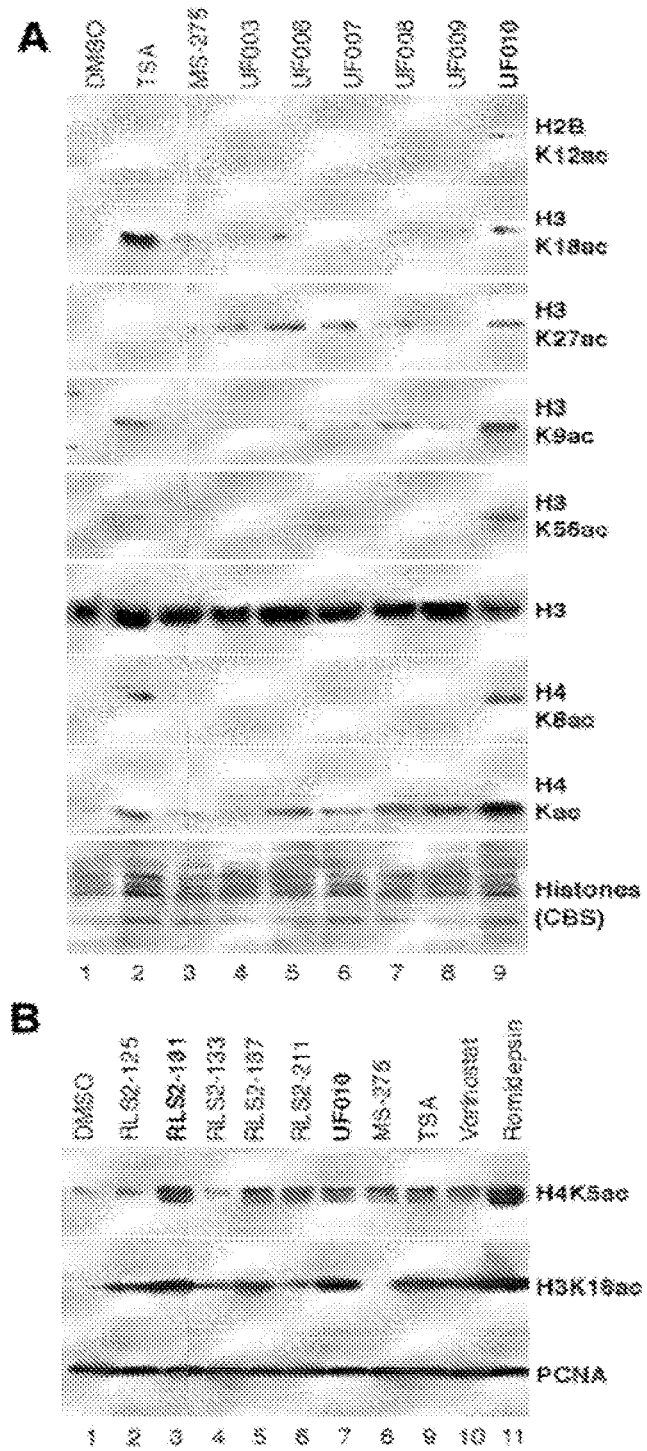
FIG. 1. depicts (A) the levels of acetylated histones at various histone sites (e.g., H2BK12ac, H3K18ac, H3K27ac, H3K9ac, H3K56ac, H3, H4K8ac, H4Kac, H4K5ac, and H3K18ac) in HCT116 cells upon exposure to Trichostatin A (TSA, 0.2 µM) and 2 µM of MS-275, UF003, UF006, UF007, UF008, UF009, and UF010 for 1 h. Histones were extracted and subject to Western Blotting (WB) with antibodies to histones with the indicated modifications or stained with colloidal blue (CBS). The antibodies against H4Kac recognize H4 acetylated at K5, 8, 12 and 16.

In order that the invention may be more readily understood, certain terms are first defined here for convenience.

As used herein, the term "treating" a disorder encompasses preventing, ameliorating, mitigating and/or managing the disorder and/or conditions that may cause the disorder. The terms "treating" and "treatment" refer to a method of alleviating or abating a disease and/or its attendant symptoms. In accordance with the present invention "treating" includes preventing, blocking, inhibiting, attenuating, protecting against, modulating, reversing the effects of and reducing the occurrence of e.g., the harmful effects of a disorder.

As used herein, "inhibiting" encompasses preventing, reducing and halting progression.

The term "modulate" refers to increases or decreases in the activity of a cell in response to exposure to a compound of the invention.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A "peptide" is a sequence of at least two amino acids. Peptides can consist of short as well as long amino acid sequences, including proteins.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "protein" refers to series of amino acid residues connected one to the other by peptide bonds between the alpha-amino and carboxy groups of adjacent residues.

Amino acids may be referred to herein by either their commonly known three letter symbols or by the one-letter symbols recommended by the IUPAC-IUB Biochemical Nomenclature Commission.

As to amino acid sequences, one of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

Macromolecular structures such as polypeptide structures can be described in terms of various levels of organization. For a general discussion of this organization, see, e.g., Alberts et al., Molecular Biology of the Cell (3rd ed., 1994) and Cantor and Schimmel, Biophysical Chemistry Part I. The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the elastase inhibitor compound are outweighed by the therapeutically beneficial effects.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The term "therapeutically effective amount" refers to that amount of the compound being administered sufficient to prevent development of or alleviate to some extent one or more of the symptoms of the condition or disorder being treated.

A therapeutically effective amount of compound (i.e., an effective dosage) may range from about 0.005 µg/kg to about 200 mg/kg, preferably about 0.1 mg/kg to about 200 mg/kg, more preferably about 10 mg/kg to about 100 mg/kg of body weight. In other embodiments, the therapeutically effect amount may range from about 1.0 µM to about 500 nM. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments. In one example, a subject is treated with a compound in the range of between about 0.005 µg/kg to about 200 mg/kg of body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of a compound used for treatment may increase or decrease over the course of a particular treatment.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", J. Pharm. Sci. 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included. In aspects, the compounds of the invention are prodrugs of any of the formulae herein.

The term "subject" refers to animals such as mammals, including, but not limited to, primates (e.g., humans), cows, sheep, goats, horses, dogs, cats, rabbits, rats, mice and the like. In certain embodiments, the subject is a human.

Furthermore the compounds of the invention include olefins having either geometry: "Z" refers to what is referred to as a "cis" (same side) conformation whereas "E" refers to what is referred to as a "trans" (opposite side) conformation. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl radical.

As used herein, the term "halogen", "hal" or "halo" means —F, —Cl, —Br or —I.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofuranyl, tetrahydrothienyl, thiirenyl, and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I–, Cl–, Br–, F–), hydroxy, alkoxy (e.g., —OMe, —O-t-Bu), acyloxy anions (e.g., —OAc, —OC(O)CF$_3$), sulfonates (e.g., mesyl, tosyl), acetamides (e.g., —NHC(O)Me), carbamates (e.g., N(Me)C(O)Ot-Bu), phosphonates (e.g., —OP(O)(OEt)$_2$), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy.

Compounds of the Invention

Compounds of the invention can be made by means known in the art of organic synthesis. Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis, 2$^{nd}$ Edition*, Carlson R, Ed, 2005; Elsevier Science Ltd.; Jahnisch, K et al, Angew. Chem. Int. Ed. Engl. 2004 43: 406; and references therein). Additional reaction schemes and protocols may be determined by the skilled artesian by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases such as the US Patent and Trademark Office text database.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. Also embodied are extracts and fractions comprising compounds of the invention. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with an enantiomerically enriched compound, a racemate, or a mixture of diastereomers.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the invention is administered to cells or a subject.

Methods of Treatment

The invention is directed towards macrocyclic compounds, and methods of treating disease and disorders using the compounds or compositions thereof delineated herein.

In other aspects, the invention provides a method of treating a subject suffering from or susceptible to HDAC related disorder or disease, wherein the subject has been identified as in need of treatment for a HDAC related disorder or disease, comprising administering to said subject in need thereof, an effective amount of a compound or pharmaceutical composition of any of the formulae delineated herein (e.g., formula I or formula II), such that said subject is treated for said disorder. Identifying a subject in need of such treatment can be in the judgment of a subject or a health care professional and can be subjective (e.g. opinion) or objective (e.g. measurable by a test or diagnostic method).

In one aspect, the invention provides a method of modulating the proliferation activity of a cell in a subject, comprising contacting the subject with a compound of any of the formulae delineated herein (e.g., formula I or formula II), in an amount and under conditions sufficient to modulate cell proliferation activity.

In one embodiment, the modulation is inhibition.

In another aspect, the invention provides a method of treating a subject suffering from or susceptible to a cell proliferation related disorder or disease, comprising administering to the subject an effective amount of a compound or pharmaceutical composition of any of the formulae delineated herein (e.g., formula I or formula II).

In other aspects, the invention provides a method of treating a subject suffering from or susceptible to a cell proliferation related disorder or disease, wherein the subject has been identified as in need of treatment for a cell proliferation related disorder or disease, comprising administering to said subject in need thereof, an effective amount of a compound or pharmaceutical composition of any of the formulae delineated herein (e.g., formula I or formula II), such that said subject is treated for said disorder.

In certain embodiments, the invention provides a method of treating a disorder, wherein the disorder is cancer (e.g., breast, colon) or solid tumor.

In certain embodiments, the subject is a mammal, preferably a primate or human.

In another embodiment, the invention provides a method as described above, wherein the effective amount of the compound of formula I ranges from about 0.005 μg/kg to about 200 mg/kg. In certain embodiments, the effective amount of the compound of formula I ranges from about 0.1 mg/kg to about 200 mg/kg. In a further embodiment, the effective amount of compound of formula I ranges from about 10 mg/kg to 100 mg/kg.

In other embodiments, the invention provides a method as described above wherein the effective amount of the compound of formula I ranges from about 1.0 μM to about 500 nM. In certain embodiments, the effective amount ranges from about 10.0 μM to about 1000 μM. In another embodiment, the effective amount ranges from about 1.0 nM to about 10 nM.

In another embodiment, the invention provides a method as described above, wherein the compound of any of the formulae delineated herein (e.g., formula I or formula II) is administered intravenously, intramuscularly, subcutaneously, intracerebroventricularly, orally or topically.

In another embodiment, the invention provides a method as described herein wherein the compound of any of the formulae delineated herein (e.g., formula I or formula II) demonstrates selectivity (e.g., at least 2-fold, at least 5-fold, at least 10-fold, at least X-fold where X is any number between 1 and 20 inclusive) in cell growth activity (e.g., in transformed/nontransformed, MDA-MB-231/NMuMG, U20S/NIH3T3 cells). In another aspect, the compound of any of the formulae delineated herein (e.g., formula I or formula II) demonstrates selectivity in modulating cell growth activity (e.g., at least 2-fold, at least 5-fold, at least 10-fold, at least X-fold where X is any number between 1 and 20 inclusive) relative to another standard anticancer therapy (e.g., paclitaxel, actinomycin D, doxorubicin).

In other embodiments, the invention provides a method as described above, wherein the compound of any of the formulae delineated herein (e.g., formula I or formula II) is administered alone or in combination with one or more other therapeutics. In a further embodiment, the additional therapeutic agent is an anti-cancer agent, chemotherapeutic agent, an anti-angiogenesis agent, cytotoxic agent, or an anti-proliferation agent. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, vincristine, vinblastine, etoposide, trimetrexate, teniposide, cisplatin and diethylstilbestrol (DES). See, generally, The Merck Manual of Diagnosis and Therapy, 15th Ed., pp. 1206-1228, Berkow et al., eds., Rahay, N.J., 1987).

Another object of the present invention is the use of a compound as described herein (e.g., of any formulae herein) in the manufacture of a medicament for use in the treatment of a cell proliferation disorder or disease, or to affect cell differentiation, dedifferentiation or transdifferentiation. Another object of the present invention is the use of a compound as described herein (e.g., of any formulae herein) for use in the treatment of a cell proliferation disorder or disease, or affect cell differentiation, dedifferentiation or transdifferentiation.

Pharmaceutical Compositions

In one aspect, the invention provides a pharmaceutical composition comprising the compound of any of the formulae delineated herein (e.g., formula I or formula II) and a pharmaceutically acceptable carrier.

In another embodiment, the invention provides a pharmaceutical composition further comprising an additional therapeutic agent. In a further embodiment, the additional therapeutic agent is an anti-cancer agent, chemotherapeutic agent, an anti-angiogenesis agent, cytotoxic agent, or an anti-proliferation agent.

In one aspect, the invention provides a kit comprising an effective amount of a compound of any of the formulae delineated herein (e.g., formula I or formula II), in unit dosage form, together with instructions for administering the compound to a subject suffering from or susceptible to a HDAC mediated disease or disorder.

In one aspect, the invention provides a kit comprising an effective amount of a compound of any of the formulae delineated herein (e.g., formula I or formula II), in unit dosage form, together with instructions for administering the compound to a subject suffering from or susceptible to a cell proliferation disease or disorder, including cancer, solid tumor, angiogenesis, etc.

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)).

Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The invention also provides a pharmaceutical composition, comprising an effective amount a compound described herein and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic (or unacceptably toxic) to the patient.

In use, at least one compound according to the present invention is administered in a pharmaceutically effective amount to a subject in need thereof in a pharmaceutical carrier by intravenous, intramuscular, subcutaneous, or intracerebro ventricular injection or by oral administration or topical application. In accordance with the present invention, a compound of the invention may be administered alone or in conjunction with a second, different therapeutic. By "in conjunction with" is meant together, substantially simultaneously or sequentially. In one embodiment, a compound of the invention is administered acutely. The compound of the invention may therefore be administered for a short course of treatment, such as for about 1 day to about 1 week. In another embodiment, the compound of the invention may be administered over a longer period of time to ameliorate chronic disorders, such as, for example, for about one week to several months depending upon the condition to be treated.

By "pharmaceutically effective amount" as used herein is meant an amount of a compound of the invention, high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, the nature of concurrent therapy and the specific organozinc compound employed. For example, a therapeutically effective amount of a compound of the invention administered to a child or a neonate will be reduced proportionately in accordance with sound medical judgment. The effective amount of a compound of the invention will thus be the minimum amount which will provide the desired effect.

A decided practical advantage of the present invention is that the compound may be administered in a convenient manner such as by intravenous, intramuscular, subcutaneous, oral or intra-cerebroventricular injection routes or by topical application, such as in creams or gels. Depending on the route of administration, the active ingredients which comprise a compound of the invention may be required to be coated in a material to protect the compound from the action of enzymes, acids and other natural conditions which may inactivate the compound. In order to administer a compound of the invention by other than parenteral administration, the compound can be coated by, or administered with, a material to prevent inactivation.

The compound may be administered parenterally or intraperitoneally. Dispersions can also be prepared, for example, in glycerol, liquid polyethylene glycols, and mixtures thereof, and in oils.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage. The carrier can be a solvent or dispersion medium containing, for example, water, DMSO, ethanol, polyol (for example, glycerol, propylene glycol, liquid polyethylene glycol, and the like), suitable mixtures thereof and vegetable oils. The proper fluidity can be maintained, for example, by the use of a coating such as lecithin, by the maintenance of the required particle size in the case of dispersion. In many cases it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the compound of the invention in the required amount in the appropriate solvent with various other ingredients enumerated above, as required, followed by filtered sterilization. Generally, dispersions are prepared by incorporating the various sterilized compounds into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yields a powder of the active ingredient plus any additional desired ingredient from previously sterile-filtered solution thereof.

For oral therapeutic administration, the compound may be incorporated with excipients and used in the form of ingestible tablets, buccal tablets, troches, capsules, elixirs, suspensions, syrups, wafers, and the like. Compositions or preparations according to the present invention are prepared so that an oral dosage unit form contains compound concentration sufficient to treat a disorder in a subject.

Some examples of substances which can serve as pharmaceutical carriers are sugars, such as lactose, glucose and sucrose; starches such as corn starch and potato starch; cellulose and its derivatives such as sodium carboxymethycellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of theobroma; polyols such as propylene glycol, glycerine, sorbitol, manitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tableting agents, stabilizers, anti-oxidants and preservatives, can also be present.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

EXAMPLES

The present invention will now be demonstrated using specific examples that are not to be construed as limiting.

Example 1: Identification of UF010

A high-throughput screening (HTS) campaign of the 622,360 compounds in the Scripps Drug Discovery Library was conducted using a luciferase reporter under the control of the adenovirus (Ad) major late promoter (Ad-MLP-Luc) in the colon cancer HCT116 cell line as the primary screen. Compared to the luciferase reporter under the control of the Ad E2 early promoter (Ad-E2-Luc), the Ad-MLP-Luc reporter activity was dramatically increased in a dose-dependent manner by HDACi romidepsin or vorinostat. The similar observed responses of the Ad-MLP-Luc reporter to different classes of HDACi indicate that HDAC inhibition is the primary mechanism for the reporter activation. Each library compound was assayed at a single point at the dose of 8.6 µM. The reporter activity was detected as luminescence readout and cell viability was monitored with the PrestoBlue dye as fluorescence intensity in a multiplex format. The viability counterscreen assay was used to remove highly toxic compounds. The HTS assays were robust with Z' of >0.6. A specific hit-cutoff based on an average plus 3-fold SD was applied, resulting in the identification of 5,868 compounds that increased the Ad-MLP-Luc activity by 9.2% of the high control (vorinostat at 28 µM). These compounds were tested in confirmation assays in triplicate at 8.6 µM, among which 1,575 compounds were confirmed to activate the Ad-MLP-Luc. The top 637 compounds were further tested in 10-point dose response in triplicate in the Ad-MLP-Luc activation assay. We then selected 315 compounds highly active in the cell-based assays for in vitro HDAC1 inhibition assays and artifact assays using the HDAC/II-Glo reagents. A majority (54%) of these compounds inhibited HDAC1 in vitro with a potency of <10 µM, among which there are 9 hydroxamates, including vorinostat and scriptaid, 7 benzamides, and benzhydrazides (e.g., UF010). These results highlight the robustness of the cell-based Ad-MLP-Luc activation assays for identifying potent HDACi.

UF010 was screened against all $Zn^{2+}$-dependent HDACs and profiled as a class I HDAC-selective inhibitor with sub-micromolar potencies against HDACs 1, 2 and 3 (Table 1).

TABLE 1

Inhibitory Potency ($IC_{50}$, µM) of Different Classes of HDAC Inhibitors against HDAC1-11

| Inhibitor | Class | HDAC 1 | HDAC 2 | HDAC 3 | HDAC 8 | HDAC 6 | HDAC 10 | HDAC 11 | HDAC 4 | HDAC 5 | HDAC 7 | HDAC 9 |
|---|---|---|---|---|---|---|---|---|---|---|---|---|
| UF010 [a] | Benzhydrazide | 0.5 | 0.1 | 0.06 | 1.5 | 9.1 | 15.3 | 44.5 | >100 | >100 | >100 | >100 |
| MS-275 [b] | Benzamide | 0.2 | 0.5 | 0.3 | >10 | >10 | >10 | NA | >10 | >10 | >10 | >10 |
| Cpd60 [c] | Benzamide | 0.001 | 0.008 | 0.5 | >30 | >30 | 3.4 | NA | >30 | >30 | >30 | >30 |
| SAHA | hydroxamic acid | 0.06 | 0.3 | 0.02 | 0.8 | 0.009 | 0.03 | NA | >10 | >10 | >10 | >10 |
| TSA [d] | hydroxamic acid | 0.005 | 0.008 | 0.01 | 0.2 | 0.0007 | 0.04 | 0.01 | 5.0 | 2.6 | 1.4 | 10.4 |
| Romidepsin [e] | Cyclic peptide | 0.002 | 0.004 | ND | ND | 0.8 | ND | ND | 0.03 | ND | ND | ND |

[a] Dose response assays were done in the concentration range of 5 nM to 100 µM;
[b] data from (Lauffer, et al., 2013);
[c] Data from refs (Lauffer, et al., 2013; Schroeder, et al., 2013);
[d] HDAC1, and HDAC6 $IC_{50}$ data from (Lauffer, et al., 2013);
[e] Data from (Newbold, et al., 2013)

Synthesis of HDAC Inhibitors

Example 2

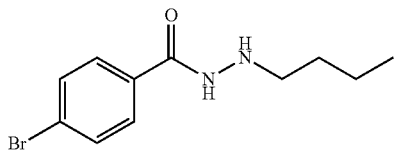

4-bromo-N'-butylbenzohydrazide (RLS2-134 or UF010)

A scintillation vial containing a Teflon-coated magnetic stir bar was charged with 4-bromobenzohydrazide (50 mg, 0.25 mmol). 1 mL of methanol, 22 µL of butyraldehyde (1 eq, 0.25 mmol) and catalytic p-toluenesulfonic acid were subsequently added to the vial. The resultant solution was allowed to stir for 12 h at room temperature. The reaction mixture was then acidified to approximately pH 5 through the addition of 4M HCl in dioxane. Sodium cyanoborohydride (19 mg, 1.2 eq, 0.31 mmol) was added and the reaction mixture was allowed to stir for 3 h at room temperature. The reaction mixture was then concentrated in vacuo. Water was added to the resultant residue followed by diethyl ether. The aqueous layer was extracted three times with diethyl ether. The organic layers were combined, dried and concentrated. The resultant white solid was further purified by flash chromatography utilizing a solvent gradient from 0-65% EtOAc in hexanes to yield 39 mg of product (58%): $^1$H NMR (400 MHz, CDCl$_3$) δ=7.65 (m, 2H), 7.59 (m, 2H), 2.94 (t, J=7.4, 2H), 1.52 (m, 2H), 1.41 (m, 2H), 0.94 (t, J=7.3, 3H). $^{13}$C NMR (100 MHz, CDCl$_3$) δ=166.7, 132.3, 132.0, 128.8, 126.88, 52.3, 30.4, 20.6, 14.3; IR (neat) 3243, 2960, 2929, 2867, 1632, 1590, 1466, 1320, 1073, 1012, 839 cm$^{-1}$; LRMS-ESI (M+H$^+$) m/z: calcd 271.2; found 271.2; HRMS (ESI) m/z calcd for C$_{11}$H$_{16}$N$_2$OBr (M+H$^+$) 271.0437, found 271.0446.

Example 3

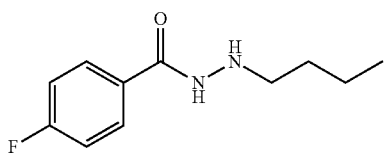

N'-butyl-4-fluorobenzohydrazide (RLS2-123)

The title compound was synthesized in a similar fashion as described for Example 2, except that 4-bromobenzohydrazide was replaced with 4-fluorobenzohydrazide. $^1$H NMR (400 MHz, CDCl$_3$) δ=7.77 (m, 2H), 7.11 (m, 2H), 2.92 (t, J=7.1, 2H), 1.51 (m, 2H), 1.39 (m, 2H), 0.91 (t, J=7.4, 3H); LRMS-ESI (M+H$^+$) m/z: calcd 211.2, found 211.2.

Example 4

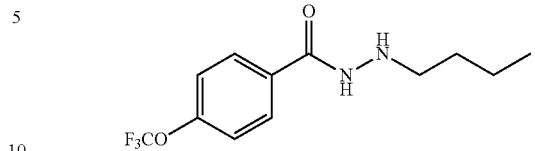

N'-butyl-4-(trifluoromethoxy)benzohydrazide (RLS2-124)

The title compound was synthesized in a similar fashion as described for Example 2, except that 4-bromobenzohydrazide was replaced with 4-(trifluoromethoxy)benzohydrazide. $^1$H NMR (400 MHz, CDCl$_3$) δ=7.80 (m, 2H), 7.26 (m, 2H), 2.92 (t, J=7.2), 1.50 (m, 2H), 1.38 (m, 2H), 0.92 (t, J=7.4, 3H); LRMS-ESI (M+H$^+$) m/z: calcd 277.3, found 277.2.

Example 5

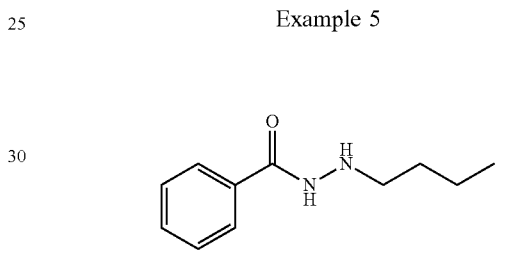

N'-butylbenzohydrazide (RLS2-125)

The title compound was synthesized in a similar fashion as described for Example 2, except that 4-bromobenzohydrazide was replaced with benzohydrazide. $^1$H NMR (400 MHz, CDCl$_3$) δ=7.75 (m, 2H), 7.47 (m, 3H), 2.93 (t, J=7.2, 2H), 1.52 (m, 2H), 1.39 (m, 2H), 0.92 (t, J=7.3, 3H). $^{13}$C NMR (100 MHz, CDCl$_3$) δ=167.6, 133.2, 132.1, 129.0, 127.2, 52.4, 30.5, 20.6, 14.3; IR (neat) 3286, 2960, 2932, 2863, 1635, 1538, 1457, 1314, 1118, 794, 692 cm$^{-1}$; LRMS-ESI (M+H$^+$) m/z: calcd 293.2; found 293.2.

Example 6

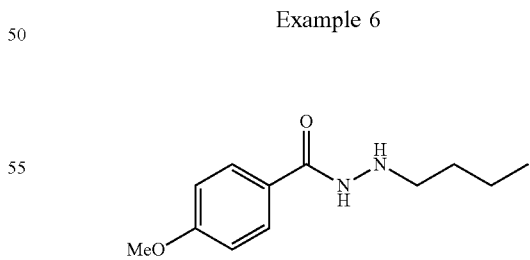

N'-butyl-4-methoxybenzohydrazide (RLS2-126)

The title compound was synthesized in a similar fashion as described for Example 2, except that 4-bromobenzohydrazide was replaced with 4-methoxybenzohydrazide. $^1$H NMR (400 MHz, CDCl$_3$) δ=7.71 (m, 2H), 6.92 (m, 2H), 3.84 (s, 3H), 2.92 (t, J=7.3, 2H), 1.52 (m, 2H), 1.40 (m, 2H), 0.93 (t, J=7.2, 3H); LRMS-ESI (M+H⁺) m/z: calcd 223.3, found 223.3.

Example 7

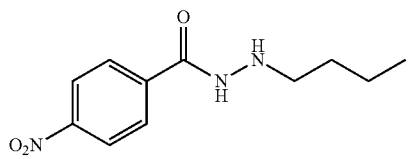

N'-butyl-4-nitrobenzohydrazide (RLS2-128)

The title compound was synthesized in a similar fashion as described for Example 2, except that 4-bromobenzohydrazide was replaced with 4-nitrobenzohydrazide.

Example 8

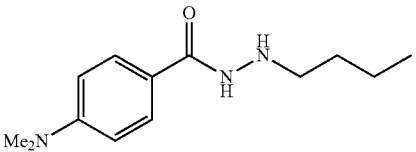 [SMILES: CCCCNNC(=O)c1ccc(OC(F)(F)F)cc1]

N'-butyl-4-(dimethylamino)benzohydrazide (RLS2-131)

The title compound was synthesized in a similar fashion as described for Example 2, except that 4-bromobenzohydrazide was replaced with 4-(dimethylamino)benzohydrazide. ¹H NMR (400 MHz, CDCl₃) δ=7.65 (m, 2H), 6.66 (m, 2H), 3.01 (s, 6H), 2.91 (t, J=7.3, 2H), 1.51 (m, 2H), 1.39 (m, 2H), 0.92 (t, J=7.3, 3H). ¹³C NMR (100 MHz, CDCl₃) δ=167.7, 153.0, 128.6, 119.8, 111.4, 52.5, 40.4, 30.5, 20.6, 14.3. IR (neat) 3282, 2957, 2928, 2860, 1606, 1521, 1443, 1366, 1304, 1204, 948, 827 cm⁻¹; LRMS-ESI (M+H⁺) m/z: calcd 236.3; found 236.3; HRMS (ESI) m/z calcd for C₁₃H₂₂N₃O (M+H⁺) 236.1763, found 236.1760.

Example 9

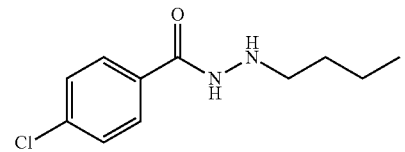

N'-butyl-4-chlorobenzohydrazide (RLS2-133)

The title compound was synthesized in a similar fashion as described for Example 2, except that 4-bromobenzohydrazide was replaced with 4-chlorobenzohydrazide. ¹H NMR (400 MHz, CDCl₃) δ=7.70 (m, 2H), 7.40 (m, 2H), 2.92 (t, J=7.1, 2H), 1.50 (m, 2H), 1.39 (m, 2H), 0.92 (t, J=7.4, 3H). ¹³C NMR (100 MHz, CDCl₃) δ=166.7, 138.4, 131.6, 129.3, 128.6, 52.3, 30.4, 20.6, 14.3; IR (neat) 3250, 2960, 2929, 2867, 1633, 1596, 1467, 1321, 1091, 1014, 841, 731 cm⁻¹; LRMS-ESI (M+H⁺) mz: calcd 227.1; found 227.2; HRMS (ESI) m/z calcd for C₁₁H₁₆N₂OCl (M+H⁺) 227.0951, found 227.0942.

Example 10

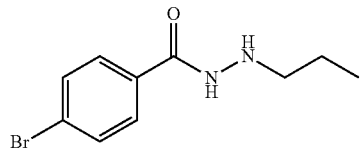

4-bromo-N'-propylbenzohydrazide (RLS2-137)

The title compound was synthesized in a similar fashion as described for Example 2, except that butyraldehyde was replaced with propionaldehyde. ¹H NMR (400 MHz, CDCl₃) δ=7.62 (m, 2H), 7.56 (m, 2H), 2.88 (t, J=7.2, 2H), 1.54 (m, 2H), 0.95 (t, J=7.4, 3H). ¹³C NMR (100 MHz, CDCl₃) δ=166.7, 132.3, 132.0, 128.8, 126.9, 54.4, 21.6, 11.9; IR (neat) 3247, 2961, 2932, 2874, 1631, 1590, 1541, 1458, 1323, 1073, 1010, 846; LRMS-ESI (M+H⁺) m/z: calcd 257.0; found 257.2 HRMS (ESI) m/z calcd for C₁₀H₁₄N₂OBr (M+H⁺) 257.0289, found 257.0288.

Example 11

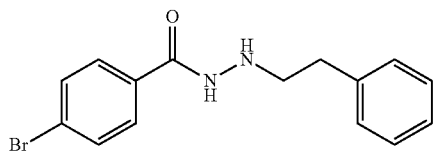 [SMILES: O=C(NNCCc1ccccc1)c1ccc(Br)cc1]

4-bromo-N'-phenethylbenzohydrazide (RLS2-138)

The title compound was synthesized in a similar fashion as described for Example 2, except that butyraldehyde was replaced with phenylacetaldehyde. ¹H NMR (400 MHz, CDCl₃) δ=7.59 (m, 4H), 7.21 (m, 5H), 2.94 (t, J=7.4, 2H), 2.69 (t, J=7.3, 2H); LRMS-ESI (M+Na+H⁺) m/z: calcd 333.2, found 333.2.

Example 12

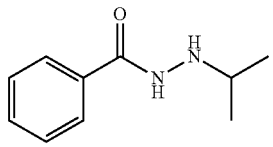

N'-isopropylbenzohydrazide (RLS2-185)

The title compound was synthesized in a similar fashion as described for Example 2, except that 4-bromobenzohydrazide was replaced with benzohydrazide and butyraldehyde was replaced with isobutyraldehyde.

Example 13

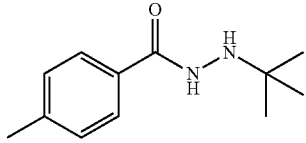

N'-tert-butyl-4-methylbenzohydrazide (RLS2-187)

The title compound was synthesized in a similar fashion as described for Example 2, except that 4-bromobenzohydrazide was replaced with 4-methylbenzohydrazide and butyraldehyde was replaced with pivalylaldehyde.

Example 14

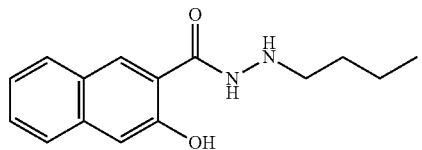 [SMILES: CCCCNNC(=O)c1cc2ccccc2cc1O]

N'-butyl-3-hydroxy-2-naphthohydrazide (RLS2-210)

The title compound was synthesized in a similar fashion as described for Example 2, except that 4-bromobenzohydrazide was replaced with 3-hydroxy-2-naphthohydrazide.

Example 15

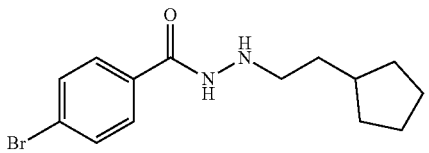 [SMILES: O=C(NNCCC1CCCC1)c1ccc(Br)cc1]

4-bromo-N'-(2-cyclopentylethyl)benzohydrazide (RLS2-219)

The title compound was synthesized in a similar fashion as described for Example 2, except that butyraldehyde was replaced with cyclopentylacetaldehyde. $^1$H NMR (400 MHz, CDCl$_3$) δ=7.65 (m, 2H), 7.55 (m, 2H), 2.94 (t, J=7.5, 2H), 1.65 (m, 11H); LRMS-ESI m/z: calcd 311.2, found 311.2; LRMS-ESI (M+H$^+$) m/z: calcd 311.2, found 311.2.

Example 16

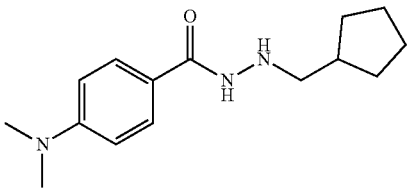 [SMILES: CN(C)c1ccc(C(=O)NNCC2CCCC2)cc1]

N'-(cyclopentylmethyl)-4-(dimethylamino)benzohydrazide (RLS2-225)

The title compound was synthesized in a similar fashion as described for Example 2, except that 4-bromobenzohydrazide was replaced with 4-(dimethylamino)benzohydrazide and butyraldehyde was replaced with cyclopentylaldehyde.

Example 17

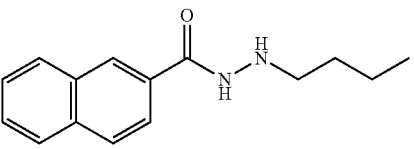 [SMILES: CCCCNNC(=O)c1ccc2ccccc2c1]

N'-butyl-2-naphthohydrazide (RLS2-238)

The title compound was synthesized in a similar fashion as described for Example 2, except that 4-bromobenzohydrazide was replaced with 2-naphthohydrazide.

Example 18

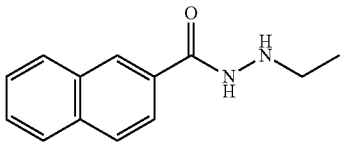 [SMILES: CCNNC(=O)c1ccc2ccccc2c1]

N'-ethyl-2-naphthohydrazide (RLS2-240)

The title compound was synthesized in a similar fashion as described for Example 2, except that 4-bromobenzohydrazide was replaced with 2-naphthohydrazide and butyraldehyde was replaced with acetaldehyde.

Example 19

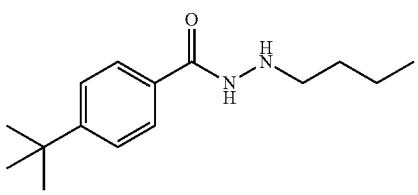 [SMILES: CCCCNNC(=O)c1ccc(C(C)(C)C)cc1]

4-tert-butyl-N'-butylbenzohydrazide (RLS2-211)

The title compound was synthesized in a similar fashion as described for Example 2, except that 4-bromobenzohydrazide was replaced with 4-tert-butylbenzohydrazide.

Example 20

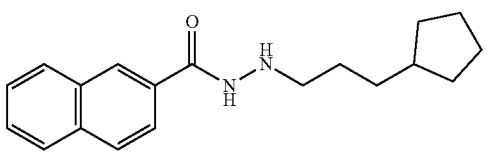 [SMILES: O=C(NNCCCC1CCCC1)c1ccc2ccccc2c1]

N'-(3-cyclopentylpropyl)-2-naphthohydrazide (RLS2-249)

The title compound was synthesized in a similar fashion as described for Example 2, except that 4-bromobenzohydrazide was replaced with 2-naphthohydrazide and butyraldehyde was replaced with 3-cyclopentylpropanal.

Example 21

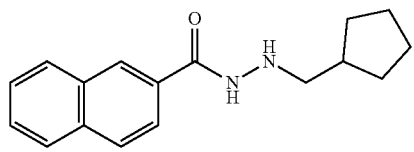 [SMILES: O=C(NNCC1CCCC1)c1ccc2ccccc2c1]

N'-(cyclopentylmethyl)-2-naphthohydrazide (RLS2-254)

The title compound was synthesized in a similar fashion as described for Example 2, except that 4-bromobenzohydrazide was replaced with 2-naphthohydrazide and butyraldehyde was replaced with cyclopentylaldehyde.

Example 22

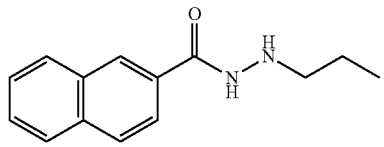 [SMILES: CCCNNC(=O)c1ccc2ccccc2c1]

N'-propyl-2-naphthohydrazide (RLS2-255)

The title compound was synthesized in a similar fashion as described for Example 2, except that 4-bromobenzohydrazide was replaced with 2-naphthohydrazide and butyraldehyde was replaced with propionaldehyde.

Example 23

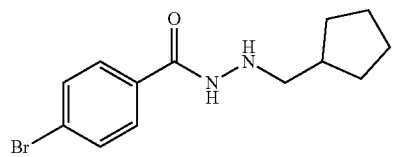 [SMILES: O=C(NNCC1CCCC1)c1ccc(Br)cc1]

4-bromo-N'-(cyclopentylmethyl)benzohydrazide (RLS2-256)

The title compound was synthesized in a similar fashion as described for Example 2, except that butyraldehyde was replaced with cyclopentylaldehyde. $^1$H NMR (400 MHz, CDCl$_3$) δ=7.63 (m, 2H), 7.57 (m, 2H), 2.88 (d, J=7.2, 2H), 1.58 (m, 9H); LRMS-ESI (M+H$^+$) m/z: calcd 297.1, found 297.2.

Example 24

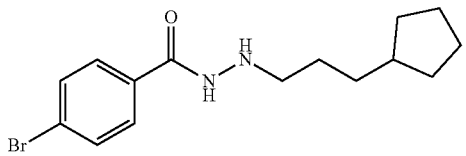 [SMILES: O=C(NNCCCC1CCCC1)c1ccc(Br)cc1]

4-bromo-N'-(3-cyclopentylpropyl)benzohydrazide (RLS2-257)

The title compound was synthesized in a similar fashion as described for Example 2, except that butyraldehyde was replaced with 3-cyclopentylpropanal. $^1$H NMR (400 MHz, CDCl$_3$) δ=7.65 (m, 2H), 7.55 (m, 2H), 2.92 (t, J=7.3, 2H), 1.39 (m, 13H). LRMS-ESI (M+H$^+$) m/z: calcd 311.2, found 311.2.

Example 25

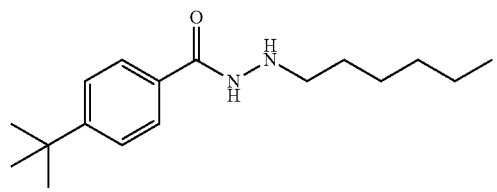 [SMILES: CCCCCCNNC(=O)c1ccc(C(C)(C)C)cc1]

4-tert-butyl-N'-hexylbenzohydrazide (RLS2-283)

The title compound was synthesized in a similar fashion as described for Example 2, except that 4-bromobenzohy-

Example 26

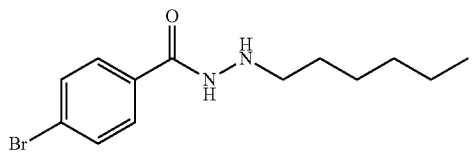 [SMILES: CCCCCCNNC(=O)c1ccc(Br)cc1]

4-bromo-N'-hexylbenzohydrazide (RLS2-284)

The title compound was synthesized in a similar fashion as described for Example 2, except that butyraldehyde was replaced with hexanal. $^1$H NMR (400 MHz, CDCl$_3$) δ=7.63 (m, 2H), 7.54 (m, 2H), 2.89 (t, J=7.4), 1.49 (m, 2H), 1.24 (m, 6H), 0.86 (m, 3H). LRMS-ESI (M+H$^+$) m/z: calcd 325.1, found 325.2.

Example 27

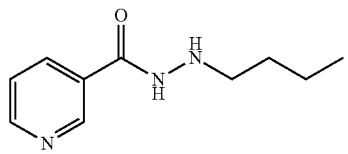

N'-butylnicotinohydrazide (RLS2-289)

The title compound was synthesized in a similar fashion as described for Example 2, except that 4-bromobenzohydrazide was replaced with nicotinohydrazide.

Example 28

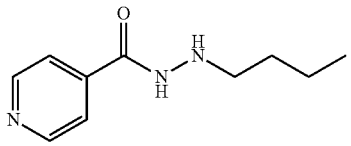

N'-butylisonicotinohydrazide (RLS2-290)

The title compound was synthesized in a similar fashion as described for Example 2, except that 4-bromobenzohydrazide was replaced with isonicotinohydrazide.

Example 29

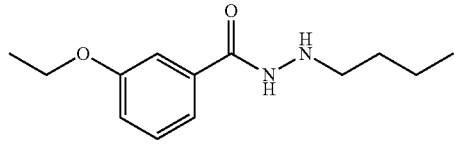 [SMILES: CCCCNNC(=O)c1cccc(OCC)c1]

N'-butyl-3-ethoxybenzohydrazide (RLS2-303)

The title compound was synthesized in a similar fashion as described for Example 2, except that 4-bromobenzohydrazide was replaced with 3-methoxybenzohydrazide.

Example 30

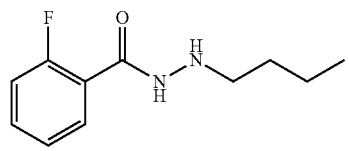

N'-butyl-2-fluorobenzohydrazide (RLS2-305)

The title compound was synthesized in a similar fashion as described for Example 2, except that 4-bromobenzohydrazide was replaced with 2-fluorobenzohydrazide.

Example 31

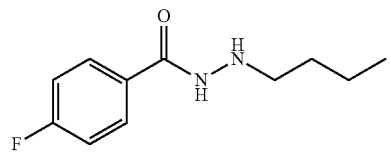

N'-butyl-4-fluorobenzohydrazide (RLS2-306)

The title compound was synthesized in a similar fashion as described for Example 2, except that 4-bromobenzohydrazide was replaced with 3-fluorobenzohydrazide.

Example 32

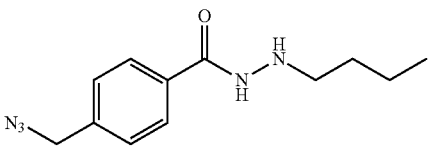 [SMILES: CCCCNNC(=O)c1ccc(CN=[N+]=[N-])cc1]

4-(azidomethyl)-N'-butylbenzohydrazide (RLS2-312)

The title compound was synthesized in a similar fashion as described for Example 2, except that 4-bromobenzohydrazide was replaced with 4-(azidomethyl)benzohydrazide. $^1$H NMR (400 MHz, CDCl$_3$) δ=7.80 (m, 2H), 7.40 (m, 2H), 4.40 (s, 2H), 2.98 (t, J=7.1, 2H), 1.54 (m, 2H), 1.40 (m, 2H), 0.92 (t, J=7.2, 3H). $^{13}$C NMR (100 MHz, CDCl$_3$) δ=167.5, 139.6, 133.2, 128.7, 127.7, 54.6, 52.4, 30.5, 20.6, 14.3; IR (neat) 3272, 2958, 2932, 2871, 2097, 1634, 1538, 1456, 1295, 850, 733; LRMS-ESI (M+H$^+$) m/z: calcd 248.1, found 248.2; HRMS (ESI) m/z calcd for C$_{12}$H$_{18}$N$_5$O (M+H$^+$) 248.1511, found 248.1502.

Example 33

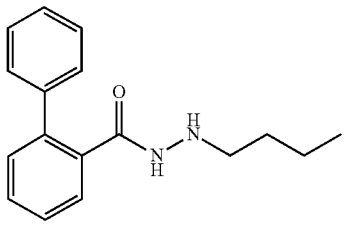 [SMILES: CCCCNNC(=O)c1ccccc1-c1ccccc1]

N'-butylbiphenyl-2-carbohydrazide (RLS3-4)

The title compound was synthesized in a similar fashion as described for Example 2, except that 4-bromobenzohydrazide was replaced with biphenyl-2-carbohydrazide.

Example 34

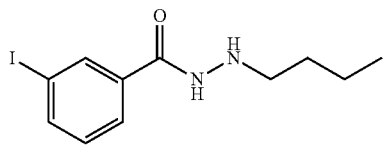

N'-butylbiphenyl-2-carbohydrazide (RLS3-5)

The title compound was synthesized in a similar fashion as described for Example 2, except that 4-bromobenzohydrazide was replaced with 3-iodo-benzohydrazide.

Example 35

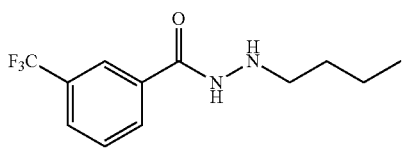 [SMILES: CCCCNNC(=O)c1cccc(C(F)(F)F)c1]

N'-butyl-3-(trifluoromethyl)benzohydrazide (RLS3-6)

The title compound was synthesized in a similar fashion as described for Example 2, except that 4-bromobenzohydrazide was replaced with 3-(trifluoromethyl)benzohydrazide.

Example 36

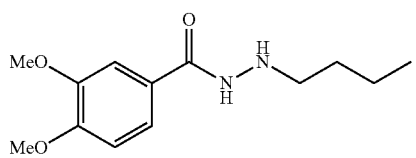 [SMILES: CCCCNNC(=O)c1ccc(OC)c(OC)c1]

N'-butyl-3,4-dimethoxybenzohydrazide (RLS3-11)

The title compound was synthesized in a similar fashion as described for Example 2, except that 4-bromobenzohydrazide was replaced with 3,4-dimethoxybenzohydrazide.

Example 37

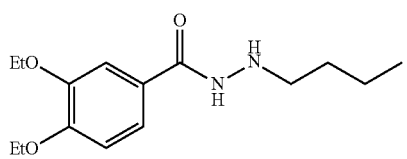 [SMILES: CCCCNNC(=O)c1ccc(OCC)c(OCC)c1]

N'-butyl-3,4-diethoxybenzohydrazide (RLS3-14)

The title compound was synthesized in a similar fashion as described for Example 2, except that 4-bromobenzohydrazide was replaced with 3,4-dimethoxybenzohydrazide.

Example 38

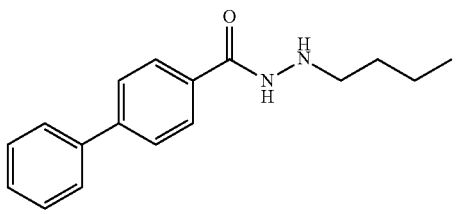 [SMILES: CCCCNNC(=O)c1ccc(-c2ccccc2)cc1]

N'-butylbiphenyl-4-carbohydrazide (RLS3-43)

The title compound was synthesized in a similar fashion as described for Example 2, except that 4-bromobenzohydrazide was replaced with biphenyl-4-carbohydrazide.

Example 39

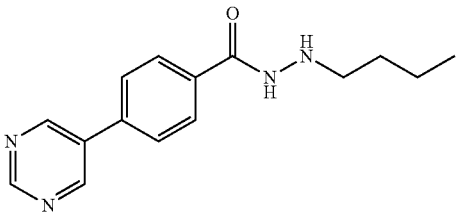 [SMILES: CCCCNNC(=O)c1ccc(-c2cncnc2)cc1]

N'-butyl-4-(pyrimidin-5-yl)benzohydrazide (SR-4369)

The title compound was synthesized in a similar fashion as described for Example 2, except that 4-bromobenzohydrazide was replaced with 4-(pyrimidin-5-yl)benzohydrazide.

Example 40

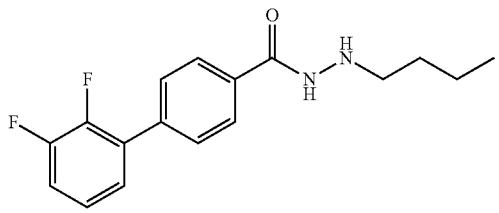 [SMILES: CCCCNNC(=O)c1ccc(-c2cccc(F)c2F)cc1]

N'-butyl-2',3'-difluorobiphenyl-4-carbohydrazide (SR-4370)

The title compound was synthesized in a similar fashion as described for Example 2, except that 4-bromobenzohydrazide was replaced with 2',3'-difluorobiphenyl-4-carbohydrazide.

Example 41

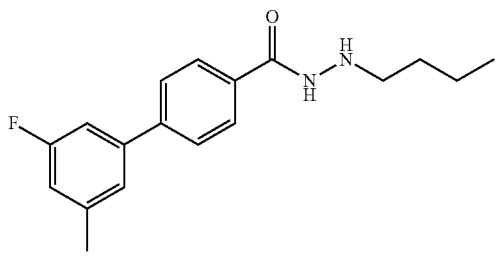 [SMILES: CCCCNNC(=O)c1ccc(-c2cc(C)cc(F)c2)cc1]

N'-butyl-3'-fluoro-5'-methylbiphenyl-4-carbohydrazide (SR-4372)

The title compound was synthesized in a similar fashion as described for Example 2, except that 4-bromobenzohydrazide was replaced with 3'-fluoro-5'-methylbiphenyl-4-carbohydrazide.

Example 42

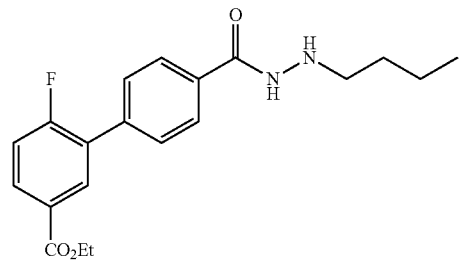 [SMILES: CCCCNNC(=O)c1ccc(-c2cc(C(=O)OCC)ccc2F)cc1]

ethyl 4'-(2-butylhydrazinecarbonyl)-6-fluorobiphenyl-3-carboxylate (SR-4373)

The title compound was synthesized in a similar fashion as described for Example 2, except that 4-bromobenzohydrazide was replaced with ethyl 6-fluoro-4'-(hydrazinecarbonyl)biphenyl-3-carboxylate.

Example 43: Cell Culture, Viability Assays, and Western Blotting

Cell lines were obtained from ATCC and cultured with Dulbecco's Modified Eagle's Medium (DMEM) supplemented with 10% bovine calf serum, penicillin to 10 units/mL, and streptomycin to 10 µg/mL. For viability assays, 5,000 cells/well were seeded in 96-well plates. Compounds or DMSO control were added 24 h later. Viability assays were done 96 h after compound addition using the CellTiter-Glo reagents (Promega). For Western blotting, cell cultures were exposed to compounds as indicated in relevant figures. Total cell lysates or isolated histones were subjected to SDS-PAGE and Western blotting essentially as described [Yang, H., Pinello, C. E., Luo, J., Li, D., Wang, Y., Zhao, L. Y., Jahn, S. C., Saldanha, S. A., Planck, J., Geary, K. R., et al. (2013). Small Molecule Inhibitors of Acetyltransferase p300 Identified by High-Throughput Screening Are Potent Anticancer Agents. Mol Cancer Tuer 12, 610-620].

Example 44: Cell Cycle Analysis and Migration Assay

MDA-MB-231 cells were treated with DMSO, UF010 or vorinostat for 24 h. Cells were fixed and subjected to cell cycle analysis using fluorescence activated cell sorting (FACS) as described [Li, Q., Zhao, L. Y., Zheng, Z., Yang, H., Santiago, A., and Liao, D. (2011). Inhibition of p53 by Adenovirus Type 12 E1B-55K Deregulates Cell Cycle Control and Sensitizes Tumor Cells to Genotoxic Agents. J Viral 85, 7976-7988]. For cell migration assays, a confluent monolayer culture of MDA-MB-231 cells were pretreated with DMSO, vorinostat or UF010 for 2 h. The cells were scratched with a pipette tip and the "wounded" areas were imaged at various time points. The denuded area was quantified using the TScratch software [Geback, T., Schulz, M. M., Koumoutsakos, P., and Detmar, M. (2009). TScratch: a novel and simple software tool for automated analysis of monolayer wound healing assays. BioTechniques 46, 265-274], and the % areas that were not covered with cells relative to the initial denuded areas were calculated.

Example 45: Gene Expression Studies

MDA-MB-231 cells were cultured in a 6-well plate. Cells were exposed in triplicate to DMSO or UF010 at 1 µM final concentration at 24 h after plating. Total RNAs were isolated from the treated cells using the RNeasy kit (Qiagen). The RNAs were then processed for microarray hybridization to the Affymetrix GeneChip Human Transcriptome Array 2.0. Data acquisition, processing and analysis are described in Supplemental Materials and Methods. For quantitative real-time PCR, the isolated RNAs were reverse transcribed using random hexamers using 2 µg RNA, the RNase inhibitor and Multiscribe reverse transcriptase (Life Technologies). The resulting cDNAs were diluted and used as input for qPCR using the SYBR green detection method. The relative levels of gene expression were determined with the ΔΔCt method.

Example 46: ShRNA Experiments

Lentiviral vectors carrying shRNA sequences against HDAC1-3 were generated in 293T cells as described [Li, Q., Zhao, L. Y., Zheng, Z., Yang, H., Santiago, A., and Liao, D.

(2011). Inhibition of p53 by Adenovirus Type 12 E1B-55K Deregulates Cell Cycle Control and Sensitizes Tumor Cells to Genotoxic Agents. J Virol 85, 7976-7988]. The cells stably or transiently transduced with these vectors were exposed to UF010 or an analog. The treated cells were subjected to viability assays as described above.

Example 47: HDAC Inhibition

Table 2 captures the HDAC inhibition activity data for select analogs. These SAR data indicate that a tripartite structure of this scaffold with a central —C(O)—NH—NH— unit flanked by a phenyl group and a short aliphatic chain increases HDAC inhibition. As for the phenyl group, the presence of a relatively bulky substituent at the para position relative to the carbonyl group also affords potent HDAC inhibitors (Table 2). Three analogs (RLS2-131, -211 and -312) displayed improved potencies vs. HDACs 1-3, among which RLS2-131 exhibited better selectivity vs. THDACs 1-3 with respect to THDAC 8 and THDAC 6 (Table 2).

TABLE 2

| Compound Number | HDAC 1 $IC_{50}$ (μM) | HDAC 2 $IC_{50}$ (μM) | HDAC 3 $IC_{50}$ (μM) | HDAC 8 $IC_{50}$ (μM) | HDAC 6 $IC_{50}$ (μM) |
|---|---|---|---|---|---|
| UF010 | 0.5 | 0.1 | 0.06 | 1.5 | 9.1 |
| RLS2-123 | 13.2 | 15.1 | 1.78 | nd | nd |
| RLS2-124 | 8.86 | 9.09 | 1.35 | nd | nd |
| RLS2-125 | >50 | >50 | >50 | nd | nd |
| RLS2-126 | 1.91 | 2.52 | 0.43 | nd | nd |
| RLS2-128 | 21.3 | 21.2 | 2.47 | nd | nd |
| RLS2-131 | 0.23 | 0.88 | 0.12 | 13.07 | >50 |
| RLS2-133 | 3.75 | 5.82 | 0.95 | nd | nd |
| RLS2-137 | 1.70 | 3.88 | 0.22 | nd | nd |
| RLS2-138 | >50 | >50 | >50 | nd | nd |
| RLS2-185 | >50 | >50 | >50 | nd | nd |
| RLS2-187 | >50 | >50 | >50 | nd | nd |
| RLS2-210 | >50 | >50 | >50 | nd | nd |
| RLS2-219 | 7.40 | 7.65 | 1.08 | nd | nd |
| RLS2-225 | 1.76 | 3.25 | 1.67 | nd | nd |
| RLS2-238 | 4.30 | 5.92 | 1.79 | nd | nd |
| RLS2-240 | >50 | >50 | >50 | nd | nd |
| RLS2-243 | >50 | >50 | >50 | nd | nd |
| RLS2-211 | 0.19 | 1.04 | 0.07 | 0.045 | 0.045 |
| RLS2-249 | >50 | >50 | >50 | nd | nd |
| RLS2-254 | >50 | >50 | >50 | nd | nd |
| RLS2-255 | 3.50 | 6.68 | 1.65 | nd | nd |
| RLS2-256 | 8.81 | 28.45 | 6.98 | nd | nd |
| RLS2-257 | >50 | >50 | >50 | nd | nd |
| RLS2-283 | 2.25 | 2.82 | 8.08 | nd | nd |
| RLS2-284 | 10.27 | 16.11 | 20.04 | nd | nd |
| RLS2-289 | 14.51 | 56.70 | 4.347 | nd | nd |
| RLS2-290 | 4.284 | 13.73 | 1.404 | nd | nd |
| RLS2-303 | >50 | >50 | >50 | nd | nd |
| RLS2-305 | 72.29 | 79.6 | 42.38 | nd | nd |
| RLS2-306 | 8.634 | 10.88 | 4.769 | nd | nd |
| RLS2-312 | 0.3199 | 0.5266 | 0.1505 | 0.886 | 0.009 |
| RLS3-4 | >50 | >50 | >50 | nd | nd |
| RLS3-5 | 31.39 | 46.95 | >50 | nd | nd |
| RLS3-6 | 35.28 | 93.33 | 1.877 | nd | nd |
| RLS3-20 | >50 | 30.05 | 13.85 | nd | nd |
| RLS3-11 | 22.2 | 20.4 | 4 | nd | nd |
| RLS3-14 | 11.8 | 7.4 | 0.8 | nd | nd |
| RLS3-43 | 0.09 | 0.8 | 0.06 | 2.43 | nd |
| SR-4369 | 1.24 | 7.27 | 2.29 | | |
| SR-4370 | 0.13 | 0.58 | 0.006 | 2.3 | 3.7 |
| SR-4372 | 0.76 | 1.2 | 0.38 | 3.6 | 3.7 |
| SR-4373 | 1.3 | 3.9 | 0.42 | 3.9 | 6.5 |

Example 48: Computer Modeling

Comparative molecular modeling studies were performed using the Schrödinger modeling package. This comparative docking study was performed without bias and in each instance the software identified the HDAC active site as the most likely binding site for the compounds disclosed herein. The $R_5$ moiety (according to Formulae I and II) of these compounds is predicted by the modeling program to fill a deep hydrophobic ("foot") pocket. This analysis also indicated that, in certain instances, the hydrazide carbonyl interacted in monodentate manner with the active site Zn, while in others the second (distal) hydrazide nitrogen was within coordination distance of the active site Zn. However, the modeling efforts indicated that 'bidentate' coordination is unlikely and, in fact, the in silico modeling indicated that certain inhibitors may not interact directly with the active site Zn. Thus, it appears that the principal mode of binding of this novel class of HDACi may not be due to strong interactions with the active site Zn, which distinguishes this class of inhibitors from the vast majority of other known HDAC inhibitors.

Example 49: Impact on Global Protein Acetylation

In cell-based assays, we exposed HCT116 cells to various compounds presented herein, including UF010. The data presented in FIG. 1(A) show that UF010 consistently induced the accumulation of acetylated histones at all sites examined. TSA strongly induced acetylation at some sites but weakly at other sites. In contrast, MS-275 only slightly induced acetylation at several sites but failed to induce acetylation at most sites. This may be due to the short (1 h) exposure of the cells to MS-275, as it and other benzamides rather slowly bind to the active site of a HDAC [Beconi, M., Aziz, O., Matthews, K., Moumne, L., O'Connell, C., Yates, D., Clifton, S., Pett, H., Vann, J., Crowley, L., et al. (2012). Oral administration of the pimelic diphenylamide HDAC inhibitor HDACi 4b is unsuitable for chronic inhibition of HDAC activity in the CNS in vivo. PloS one 7, e44498; Chou, C. J., Herman, D., and Gottesfeld, J. M. (2008). Pimelic diphenylamide 106 is a slow, tight-binding inhibitor of class I histone deacetylases. The Journal of biological chemistry 283, 35402-35409; Lauffer, B. E., Mintzer, R., Fong, R., Mukund, S., Tam, C., Zilberleyb, I., Flicke, B., Ritscher, A., Fedorowicz, G., Vallero, R., et al. (2013). Histone deacetylase (HDAC) inhibitor kinetic rate constants correlate with cellular histone acetylation but not transcription and cell viability. The Journal of biological chemistry 288, 26926-26943]. The data presented in FIG. 1(B) illustrated that UF010 and RLS2-131 consistently displayed potent inhibition of cellular HDACs.

Figure 2:
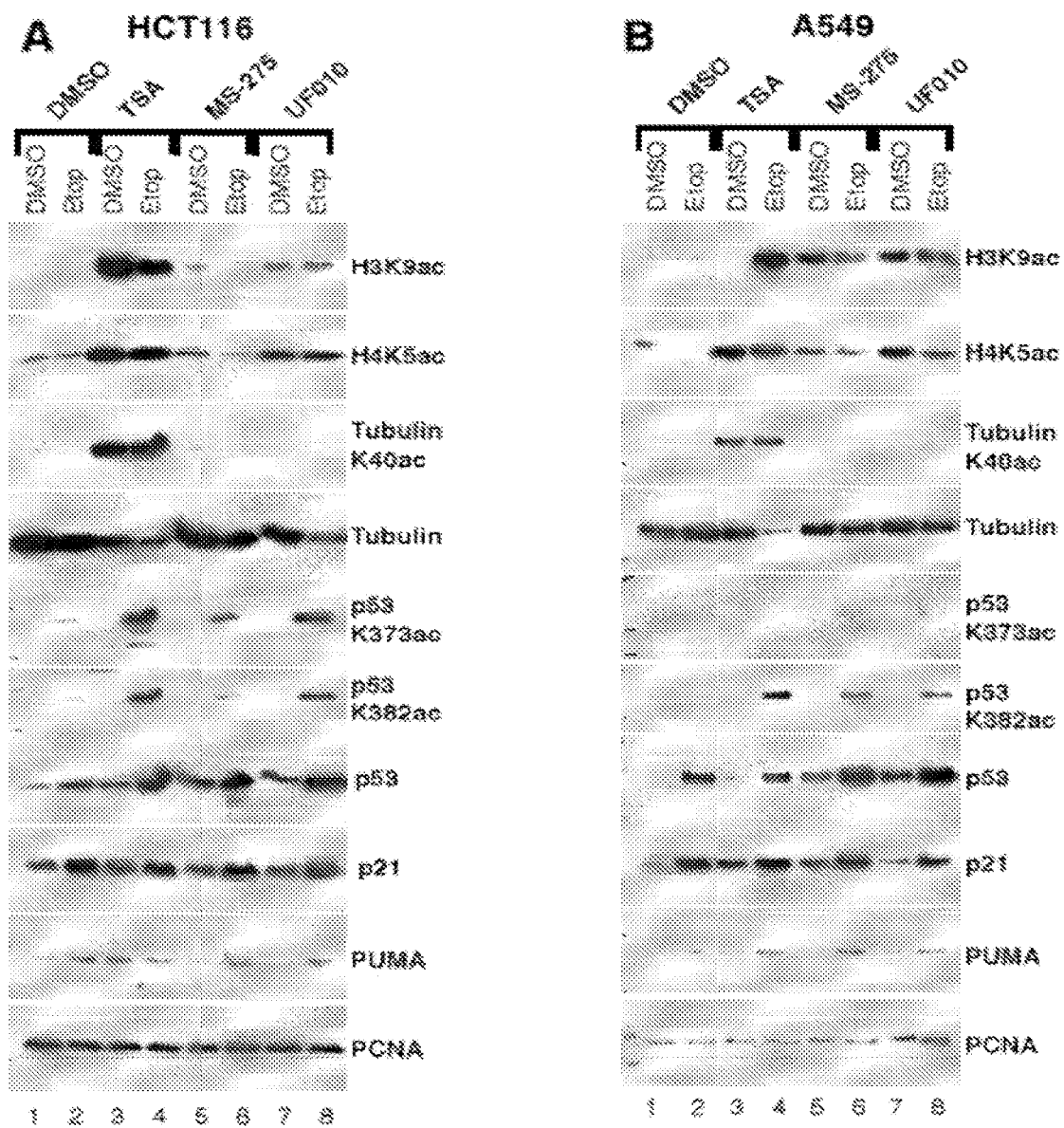
FIG. 2. depicts the levels of acetylated non-histone proteins at various acetylation sites (e.g., Tubulin K40ac, Tubulin, p53 K373ac, p53 K382ac, p53, p21, and PUMA) in (A) HCT116 cells and (B) A549 cells upon exposure for 1 h to Trichostatin A (TSA, 0.2 µM) and 2 µM of MS-275, and UF010, with and without etoposide treatment (Etop, 10 µM). The total cell lysates were subject to WB with antibodies to the indicated proteins. PCNA was detected as a loading control.

The impact of UF010 on the acetylation of non-histone proteins was also investigated in HCT116 and A549 cells (FIGS. 2(A) and 2(B)). While TSA dramatically increased α-tubulin acetylation, UF010 had little to no effect (FIGS. 2(A) and 2(B)). However, UF010 induced accumulation of acetylated p53 in both HCT116 and A549 cells after exposure to etoposide, which inhibits DNA topoisomerase II and induces double-stranded DNA breaks. As expected, etoposide activated the p53 pathway, as indicated by the accumulation of p53 and its transcriptional targets p21 and PUMA (BBC3) (FIGS. 2(A) and 2(B)). Both UF010 and MS-275 also notably stabilized p53 with or without etoposide treatment. HDAC 6, a class IIb HDAC, is the major tubulin deacetylase [Hubbert, C., Guardiola, A., Shao, R., Kawaguchi, Y., Ito, A., Nixon, A., Yoshida, M., Wang, X. F., and Yao, T. P. (2002). HDAC6 is a microtubule-associated deacetylase. Nature 417, 455-458; Matsuyama, A., Shimazu, T., Sumida, Y., Saito, A., Yoshimatsu, Y., Seigneurin-Berny, D., Osada, H., Komatsu, Y., Nishino, N., Khochbin, S., et al.

(2002). In vivo destabilization of dynamic microtubules by HDAC6-mediated deacetylation. The EMBO journal 21, 6820-6831; Zhang, Y., Li, N., Caron, C., Matthias, G., Hess, D., Khochbin, S., and Matthias, P. (2003). HDAC-6 interacts with and deacetylates tubulin and microtubules in vivo. The EMBO journal 22, 1168-1179], whereas HDAC1 deacetylates p53 [Contreras, A. U., Mebratu, Y., Delgado, M., Montano, G., Hu, C. A., Ryter, S. W., Choi, A. M., Lin, Y., Xiang, J., Chand, H., et al. (2013). Deacetylation of p53 induces autophagy by suppressing Bmf expression. The Journal of cell biology 201, 427-437; Luo, J., Su, F., Chen, D., Shiloh, A., and Gu, W. (2000). Deacetylation of p53 modulates its effect on cell growth and apoptosis. Nature 408, 377-381]. These data indicate that UF010 is a class I HDAC-selective inhibitor, in agreement with the in vitro biochemical assays (Table 1).

Figure 3:
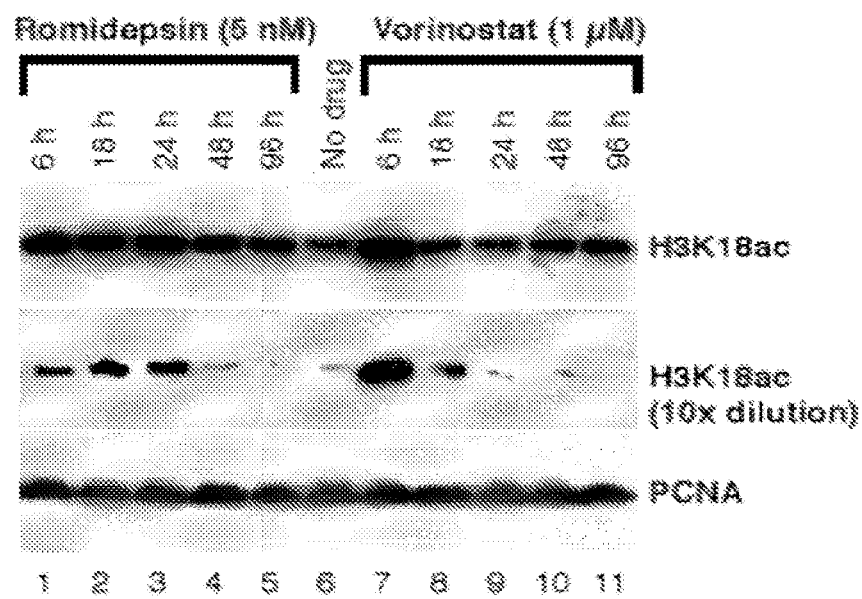
FIG. 3. depicts the rate of deacetylation of the H3K18ac site in HCT116 cells following a 6 hour pulse treatment of the HCT116 cells with Romidepsin, Vorinostat, MS-275, and UF010. The drugs were then washed out and regular medium was added. The cells were lysed at the indicated times after drug addition. The lysates were subject to WB with the indicated antibodies.
Figure 3:
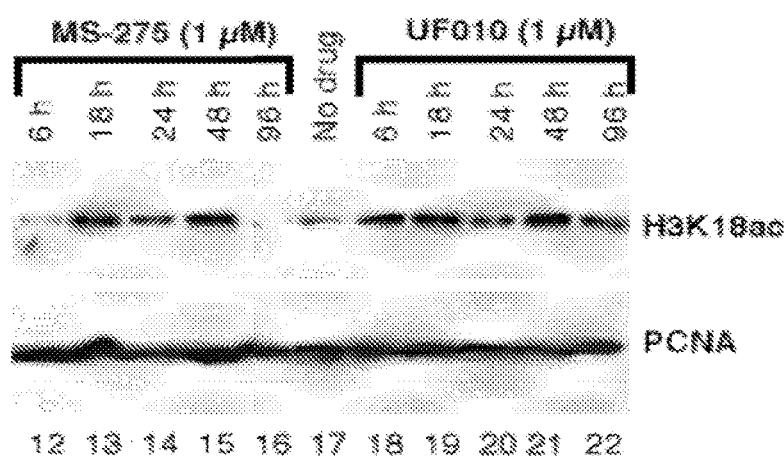

The hydroxamtes are fast-on/fast-off HDACi, whereas the benzamide HDACi display a slow-on/slow-off HDAC binding mechanism [Beconi, M., Aziz, O., Matthews, K., Moumne, L., O'Connell, C., Yates, D., Clifton, S., Pett, H., Vann, J., Crowley, L., et al. (2012). Oral administration of the pimelic diphenylamide HDAC inhibitor HDACi 4b is unsuitable for chronic inhibition of HDAC activity in the CNS in vivo. PloS one 7, e44498; Chou, C. J., Herman, D., and Gottesfeld, J. M. (2008). Pimelic diphenylamide 106 is a slow, tight-binding inhibitor of class I histone deacetylases. The Journal of biological chemistry 283, 35402-35409; Lauffer, B. E., Mintzer, R., Fong, R., Mukund, S., Tam, C., Zilberleyb, I., Flicke, B., Ritscher, A., Fedorowicz, G., Vallero, R., et al. (2013). Histone deacetylase (HDAC) inhibitor kinetic rate constants correlate with cellular histone acetylation but not transcription and cell viability. The Journal of biological chemistry 288, 26926-26943]. To assess how UF010 might interact with HDACs, we exposed HCT116 cells to various HDACi for 6 h (FIG. 3). The drugs were washed out and the cells were cultured for various lengths of time after drug washout. Consistent with published data [Lauffer, B. E., Mintzer, R., Fong, R., Mukund, S., Tam, C., Zilberleyb, I., Flicke, B., Ritscher, A., Fedorowicz, G., Vallero, R., et al. (2013). Histone deacetylase (HDAC) inhibitor kinetic rate constants correlate with cellular histone acetylation but not transcription and cell viability. The Journal of biological chemistry 288, 26926-26943], vorinostat induced high levels of histone acetylation (H3K18ac) within 6 h and the acetylated histones were quickly reduced to normal levels upon the drug removal (FIG. 3, lanes 7-11). Romidepsin also quickly induced acetylation, and the acetylation levels were stable up to 24 h (18 h after drug removal) (FIG. 3, lanes 1-5), suggesting that romidepsin has a slower rate of release from HDACs than vorinostat. The accumulation of histone acetylation induced by the benzamide MS-275 was apparent only at 18 h after the 6 h exposure, and the acetylated histones were stable up to at least 48 h (FIG. 3, lanes 12-15), in agreement with a slow-on/slow-off mode of HDAC inhibition [Beconi, M., Aziz, O., Matthews, K., Moumne, L., O'Connell, C., Yates, D., Clifton, S., Pett, H., Vann, J., Crowley, L., et al. (2012). Oral administration of the pimelic diphenylamide HDAC inhibitor HDACi 4b is unsuitable for chronic inhibition of HDAC activity in the CNS in vivo. PloS one 7, e44498; Chou, C. J., Herman, D., and Gottesfeld, J. M. (2008). Pimelic diphenylamide 106 is a slow, tight-binding inhibitor of class I histone deacetylases. The Journal of biological chemistry 283, 35402-35409; Lauffer, B. E., Mintzer, R., Fong, R., Mukund, S., Tam, C., Zilberleyb, I., Flicke, B., Ritscher, A., Fedorowicz, G., Vallero, R., et al. (2013). Histone deacetylase (HDAC) inhibitor kinetic rate constants correlate with cellular histone acetylation but not transcription and cell viability. The Journal of biological chemistry 288, 26926-26943]. For UF010, histone acetylation was induced within 6 h of exposure and the levels of induced acetylation were maintained up to 96 h (FIG. 3, lanes 17-22), suggesting that UF010 a fast-on but slow-off inhibitor.

Example 50: Antiproliferative Effects

Figure 4:
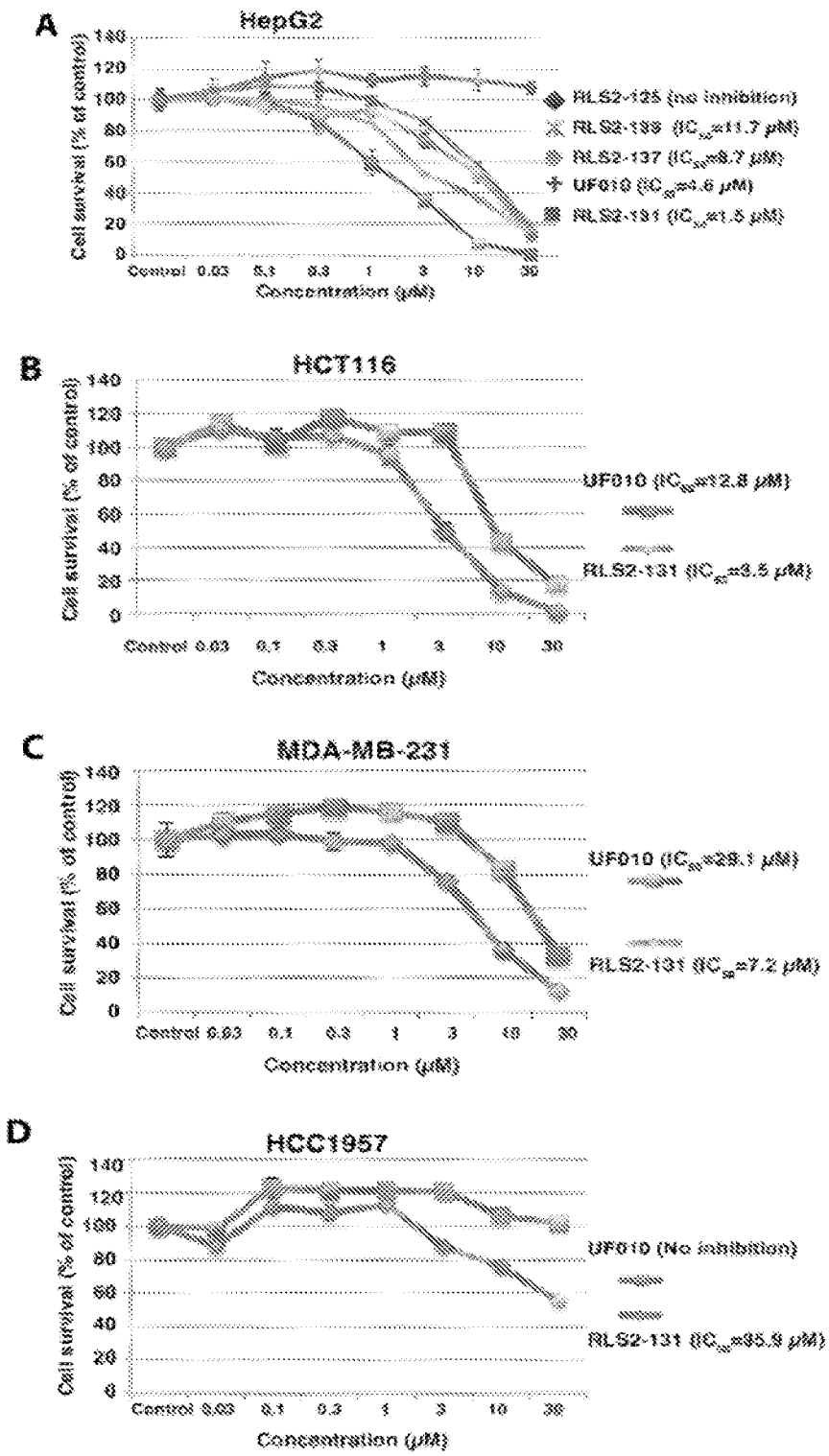
FIG. 4. depicts the exposure of (A) HepG2 cells (e.g., liver cancer), (B) HCT116 cells (colon cancer), (C) MDA-MB-231 cells (breast cancer), and (D) HCC1957 cells (breast cancer) to various doses of RLS2-125, RLS2-133, RLS2-137, UF010, and RLS2-131. Viable cells were detected at 96 h after treatment using CellTiter-Glo assay kit. The fraction of survived cells is plotted against compound concentrations. The cell killing IC50 of each compound was determined using nonlinear regression curve fitting with Prism 6 software.
Figure 5:
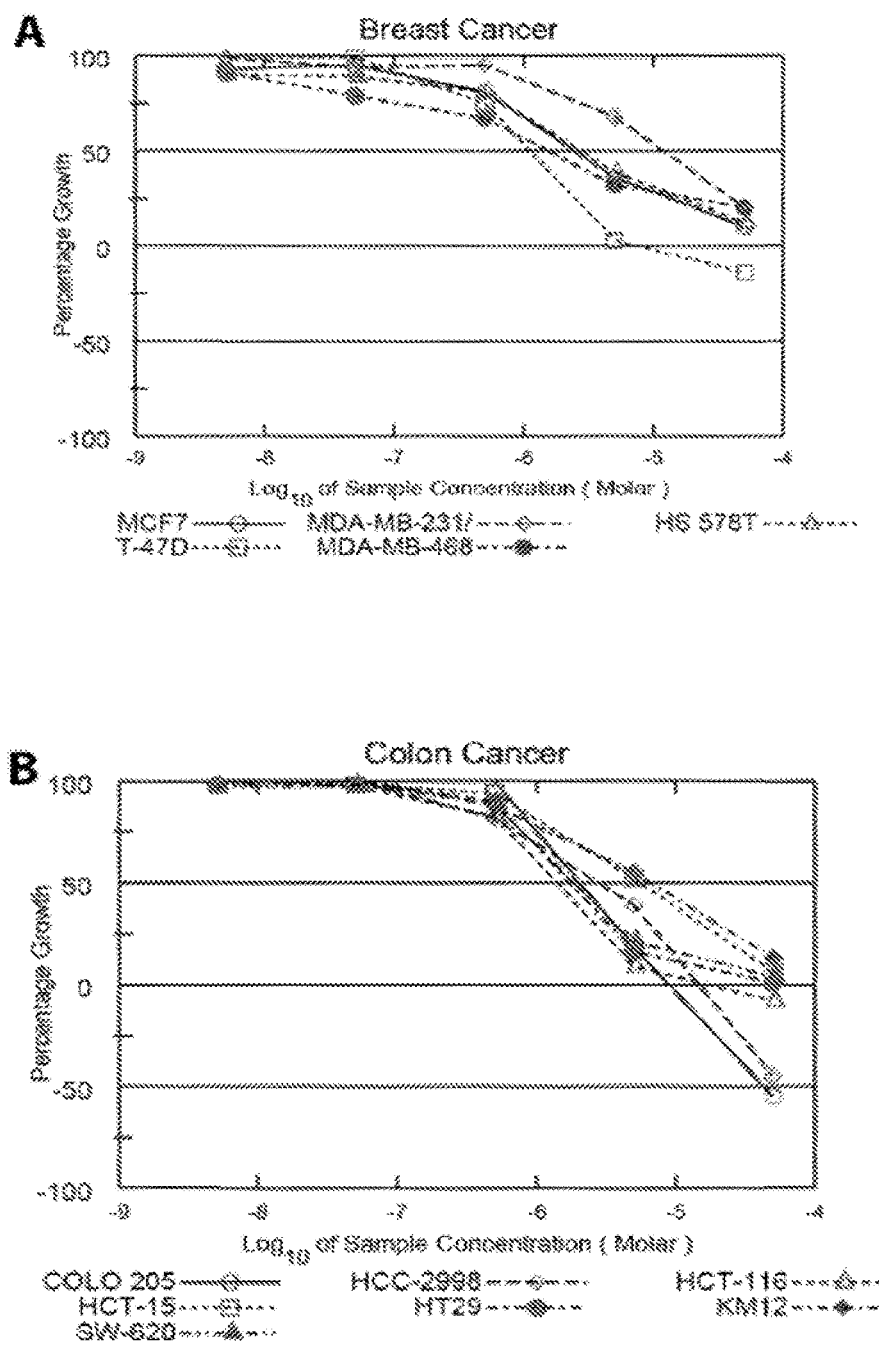
FIG. 5. depicts the exposure of (A) breast cancer cell lines (i.e., MCF7, MDA-MB-231, HS 578T, T-47D, and MDA-MB-468), (B) colon cancer cell lines (i.e., COLO 205, HCC-2998, HCT-116, HCT-15, HT29, KM12, and SW-620), (C) leukemia cell lines (i.e., CCRF-CEM, HL-60 (TB), K-562, MOLT-4, RPMI-8226, and SR), (D) non-small cell lung cancer cell lines (i.e., A549/ATCC, HOP-62, HOP-92, NCI-H226, NCI-H23, NCI-H322M, NCI-H460, and NCI-H522), (E) central nervous system cancer cell lines (i.e., SF-268, SF-295, SF-539, SNB-19, SNB-75, and U251), (F) melanoma cell lines (i.e., LOX IMVI, M14, MDA-MB-435, SK-MEL-2, SK MEL-28, SK-MEL-5, UACC-257, and UACC-62), (G) ovarian cancer cell lines (i.e., IGROV1, OVCAR-3, OVCAR-4, OVCAR-5, OVCAR-8, NCI/ADR-RES, and SK-OV-3), (H) renal cancer cell lines (i.e., 786-0, A498, ACHN, CAKI-1, RXF 393, SN12C, TK-10, and UO-31), and (I) prostate cancer cell lines (i.e., PC-3 and DU-145) from the NCI-60 panel of cancer cell lines to varying concentrations of UF010. Percent cell growth relative to the cells seeded before treatment is plotted against UF010 concentration in log scale.
Figure 5:
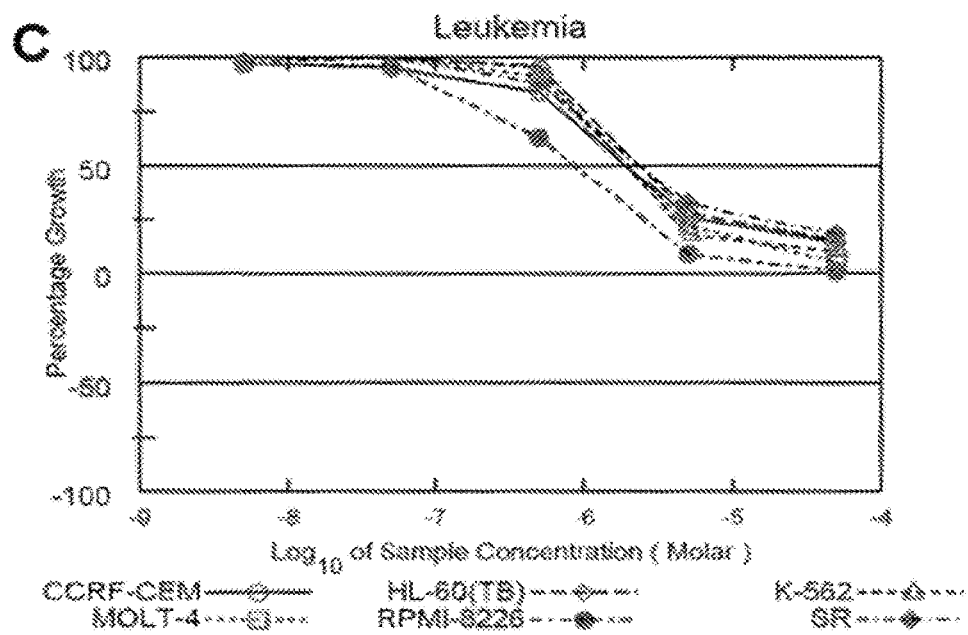
Figure 5:
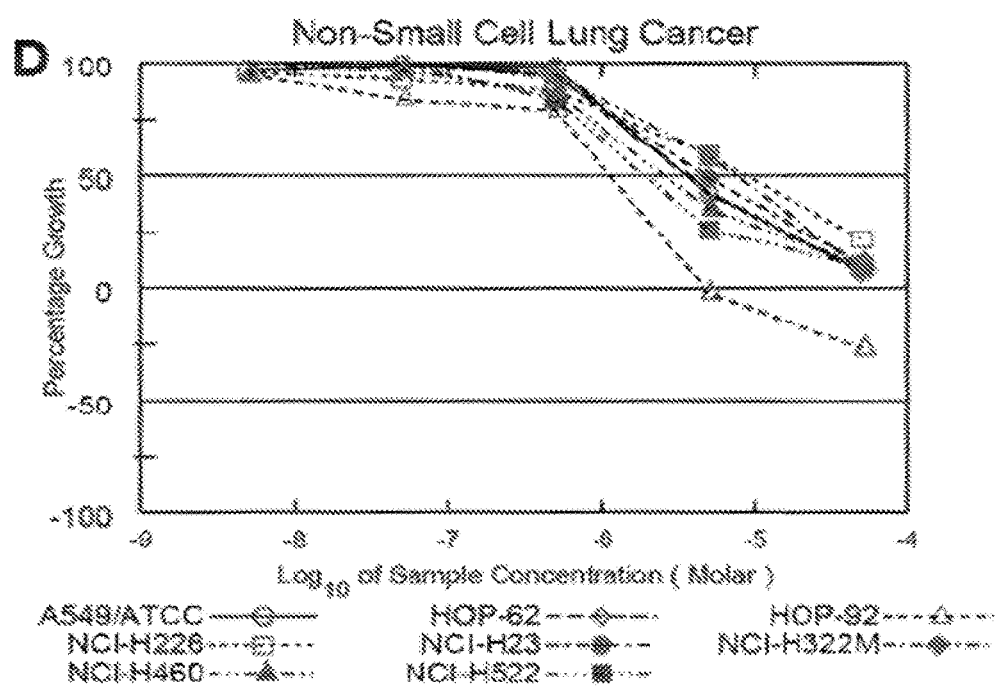
Figure 5:
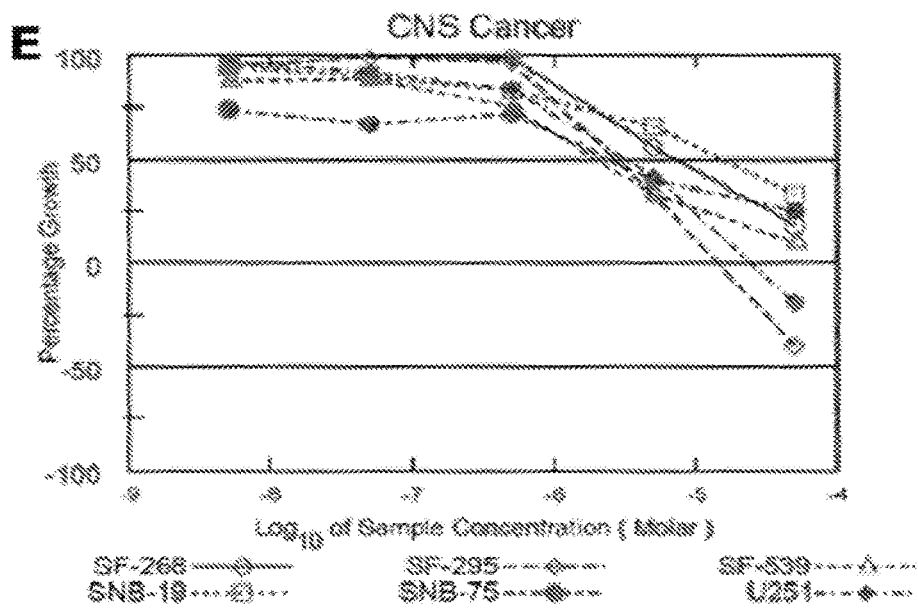
Figure 5:
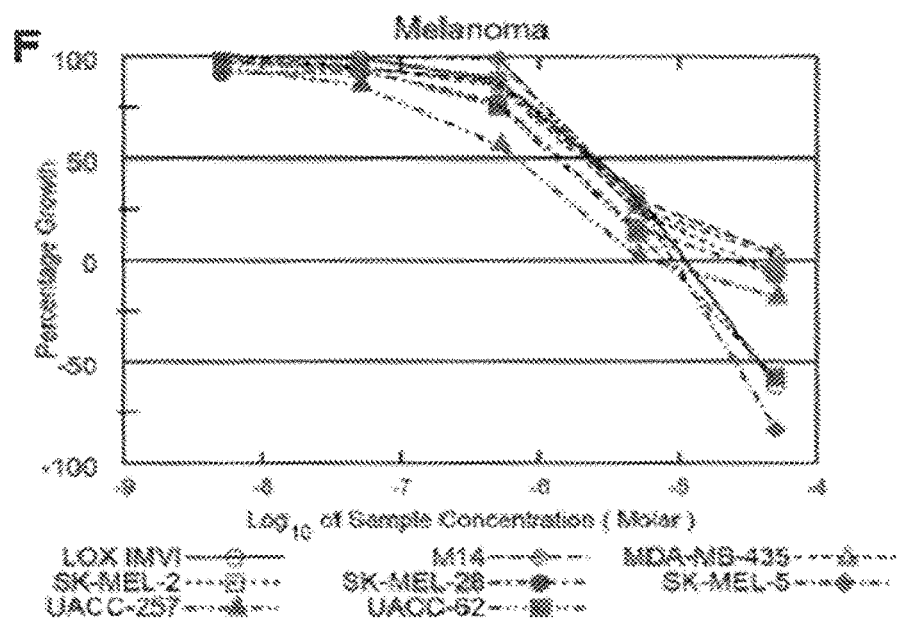
Figure 5:
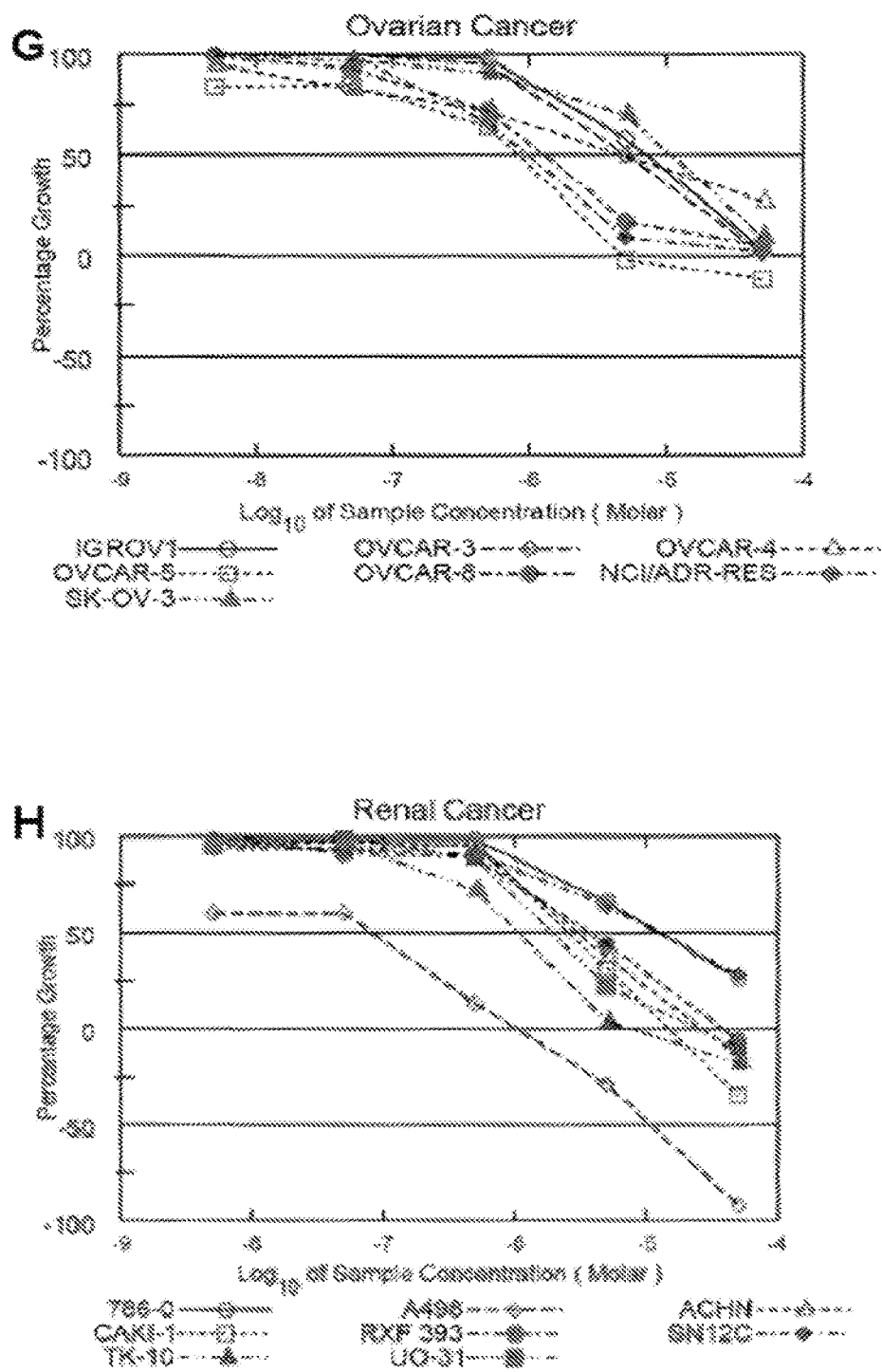
Figure 5:
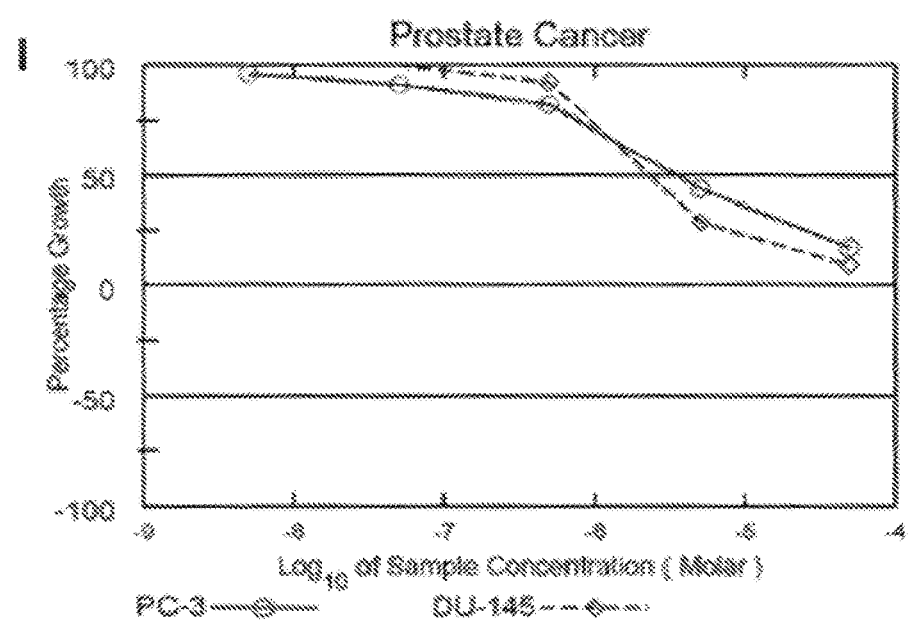

To assess the ability of the compounds to kill cancer cells, cancer cell lines were treated with various compounds, as shown in FIG. 4. Liver cancer cell line HepG2 was exposed to several compounds with various in vitro HDAC inhibition potencies. The data show that HDAC inhibition potencies of these analogs exhibited excellent correlation with their inhibition of HepG2 (FIG. 4(A)). Indeed, RLS2-131 that is 2 to 5-fold more potent than UF010 in inhibiting HDAC1, HDAC2 and HDAC3 is 3-fold more potent against HepG2. By contrast, RLS2-125 that inhibited HDACs to a lesser degree exerted little to no growth inhibition for HepG2. Similar effects were also observed in other cancer cell lines (HCT116, colon; MDA-MB-231 and HCC1957, breast cancer; FIGS. 4 (B)-(D)). These data suggest that HDAC inhibition may be one mechanism for halting cancer cell growth and proliferation. HDAC1, HDAC2 or HDAC3 were depleted with shRNAs to further examine the importance of HDACs for UF010's cellular effects. The cells with shRNA expression were treated with UF010 or RLS2-131. The data presented in Table 3 indicate that HDAC2 shRNA expression reduced UF010's cytotoxic potency by about 2-fold in both HepG2 and breast cancer MDA-MB-468 cell lines. HDAC1 depletion also reduced UF010-mediated cytotoxicity in HepG2. Similarly, depletion of HDAC1 or HDAC2 also reduced sensitivity of HepG2 cells to RLS2-131. In contrast, HDAC3 depletion markedly sensitized HepG2 cells to both UF010 and RLS2-131 (Table 3). One explanation of this may be that pharmacological HDAC3 inhibition coupled with its genetic depletion might result in a dramatic suppression of its functions, leading to a potential synthetic lethal effect. In sum, these data suggest that one mechanism that UF010 and other analogs kill cancer cells may be through pharmacological inhibition of HDACs 1-3.

TABLE 3

| $IC_{50}$ (µM) | Control | HDAC1 shRNA | HDAC2 shRNA | HDAC3 shRNA |
| --- | --- | --- | --- | --- |
| UF010 (HepG2) | 4.6 | 5.9 | 10.9 | 1.3 |
| RLS2-131 (HepG2) | 1.5 | 1.8 | 2.0 | 0.2 |
| UF010 (MDA-MB-468) | 16.1 | ND | 32.8 | nd |

Figure 6:
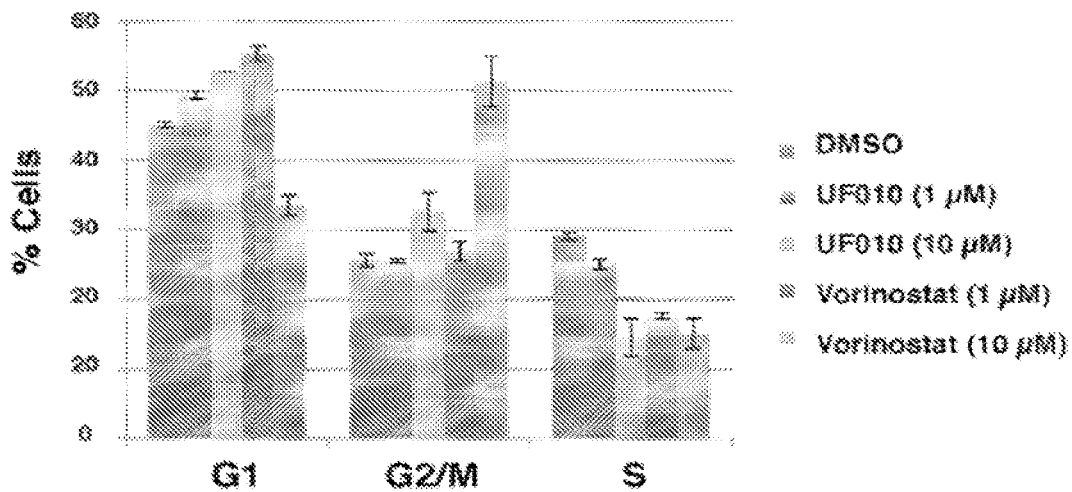
FIG. 6. depicts cell cycle analysis for MDA-MB-231 cells exposed to UF010 and SAHA (Vorinostat). MDA-MB-231 cells were exposed to DMSO (control) or the indicated doses of UF01 or SAHA for 24 h. Cells were then fixed and processed for FACS analysis. Shown are the average values of two experiments along with SEM.
Figure 7:
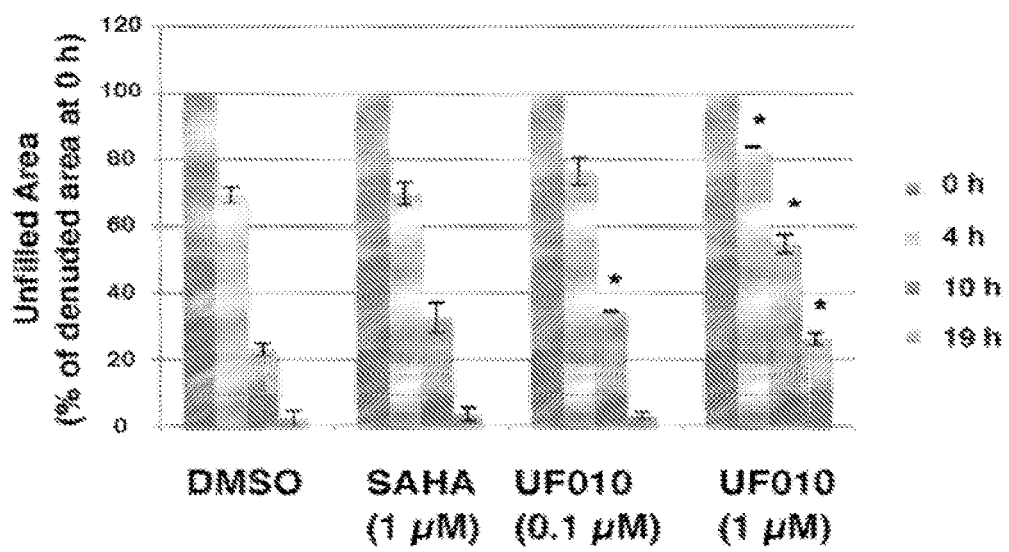
FIG. 7. depicts the cell migration to denuded areas of scratched monolayer MDA-MB-231 cultures exposed to SAHA (Vorinostat) and UF010. At 2 h after adding a compound, the monolayer cultures were scratched and the denuded areas were photographed at the indicated time points. The uncovered areas were calculated and compared to the initial open areas. Shown are averages±SEM (n=3). *: $P<0.01$ (vs. DMSO treatment).

UF010 was also screened against the NCI-60 panel of cancer cell lines. It inhibited proliferation of all tested cell lines, which include 5 breast cancer and 7 colon cancer cell lines, although sensitivity to this compound varied among these cell lines (FIGS. 5(A)-(I)). Cell cycle analysis for MDA-MB-231 cells exposed to UF010 or Vorinostat indicated that UF010 mainly blocked G1/S transition with an increased G1 cell population and a reduced cell population in the S phase in a dose-dependent manner, while vorinostat inhibited G1/S progression at 1 µM but induced a strong G2/M block at 10 µM (FIG. 6). The G2/M checkpoint induced by Vorinostat may be due to a strong DNA-damage response in cells treated with Vorinostat [Lee, J. H., Choy, M. L., Ngo, L., Foster, S. S., and Marks, P. A. (2010). Histone deacetylase inhibitor induces DNA damage, which normal but not transformed cells can repair. Proceedings of the National Academy of Sciences of the United States of America 107, 14639-14644]. To assess potential effects of UF010 on cell migration associated with metastatic progression, UF010 was profiled in a "wound" healing assays. Monolayer MDA-MB-231 cultures were exposed to DMSO, Vorinostat (SAHA) or UF010, and then scratched. Cell migration to the denuded areas was assessed. It was observed that UF010 at 1 µM markedly slowed migration, whereas SAHA did not significantly affect this phenotype (FIG. 7). Vorinostat and other hydroxamic acid HDACi have been shown to suppress breast cancer metastases in several preclinical models [Chiu, H. W., Yeh, Y. L., Wang, Y. C., Huang, W. J., Chen, Y. A., Chiou, Y. S., Ho, S. Y., Lin, P., and Wang, Y. J. (2013). Suberoylanilide hydroxamic acid, an inhibitor of histone deacetylase, enhances radiosensitivity and suppresses lung metastasis in breast cancer in vitro and in vivo. PloS one 8, e76340; Huang, W. J., Tang, Y. A., Chen, M. Y., Wang, Y. J., Hu, F. H., Wang, T. W., Chao, S. W., Chiu, H. W., Yeh, Y. L., Chang, H. Y., et al. (2013). A histone deacetylase inhibitor YCW1 with antitumor and antimetastasis properties enhances cisplatin activity against non-small cell lung cancer in preclinical studies. Cancer letters; Palmieri, D., Lockman, P. R., Thomas, F. C., Hua, E., Herring, J., Hargrave, E., Johnson, M., Flores, N., Qian, Y., Vega-Valle, E., et al. (2009). Vorinostat inhibits brain metastatic colonization in a model of triple-negative breast cancer and induces DNA double-strand breaks. Clinical cancer research: an official journal of the American Association for Cancer Research 15, 6148-6157], although other studies showed that HDACi of the hydroxamatic acid class could augment metastatic spread of certain cancer cell lines [Lin, K. T., Wang, Y. W., Chen, C. T., Ho, C. M., Su, W. H., and Jou, Y. S. (2012). HDAC inhibitors augmented cell migration and metastasis through induction of PKCs leading to identification of low toxicity modalities for combination cancer therapy. Clinical cancer research: an official journal of the American Association for Cancer Research 18, 4691-4701].

Example 51: Tumor Suppression

Figure 8:
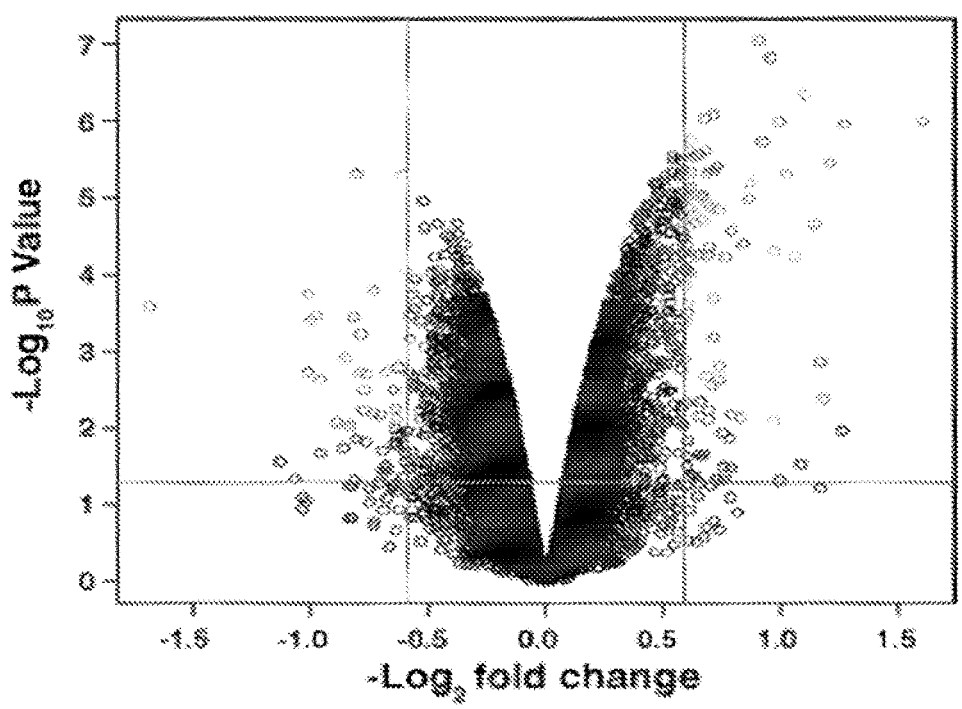
FIG. 8. depicts the global gene expression of MDA-MB-231 cells treated with UF010 at 1 µM for 24 hours and analyzed using the Affymetrix Human Transcriptome Array 2.0. RNAs were isolated and subject to microarray gene expression profiling. The two red vertical lines in the volcano plot demark 0.585 of the x-axis to indicate genes that were up- or downregulated by 1.5-fold. The red horizontal line indicates −1.3 of the y-axis for P value <0.05.

MDA-MB-231 cells were treated with UF010 at 1 µM for 24 h to analyze its impact on global gene expression in comparison to DMSO control using the Affymetrix Human Transcriptome Array 2.0, which allows for the interrogation of transcripts for splicing variants of coding and noncoding genes. The expression of a large number of transcripts was impacted due to UF010 treatment, with more downregulated transcripts than upregulated ones (FIG. 8). Most of these responsive genes exhibited moderate levels of changes in their mRNA expression. Among the responsive genes that were up or downregulated by 1.5-fold, 115 were upregulated and 68 downregulated (FIG. 8). The changes in gene expression patterns due to UF010 treatment were analyzed using Ingenuity Pathway Analysis. In the Biological Function analysis, the most highly affected pathways include the induction of cell death, the suppression of cell cycle progression and DNA repair (Table 4). In the Upstream Regulator analysis, UF010 induced the activation of p53 and Rb tumor suppressor pathways but suppressed the MYC, MYCN, and KRAS oncogenic pathways.

TABLE 4

Perturbation of Selected Cellular Pathways in MDA-MB-231 cells by UF010

| Biological Functions | | | | Upstream Regulators | | | |
| --- | --- | --- | --- | --- | --- | --- | --- |
| Category | Functional annotation | P value | Predicated activation state | Category | Molecule Type | P value | Predicated activation state |
| Cell growth and proliferation | Proliferation of cells | 6.74E−20 | Suppressed | TP53 | Transcription regulator | 1.28E−15 | Activated |
| Cell death and survival | Apoptosis | 3.21E−17 | Activated | Cisplatin | Chemical drug | 3.85E−10 | Activated |
| Gene expression | Transcription of RNA | 4.20E−16 | Suppressed | Tributyrin (butyrate) | Chemical drug | 9.30E−8 | Activated |
| Cell death and survival | Necrosis | 3.38E−14 | Activated | Rb1 | Transcription regulator | 1.07E−7 | Activated |
| Cell cycle | Cell cycle progression | 2.69E−11 | Suppressed | fulvestrant | Chemical drug | 4.41E−7 | Activated |
| DNA replication, recombination and repair | Repair of DNA | 4.06E−10 | Suppressed | Myc | Transcription regulator | 6.93E−7 | Suppressed |
| Cell death and survival | Cell survival | 1.01E−9 | Suppressed | KRAS | Enzyme | 2.11E−5 | Suppressed |
| | | | | Trichostatin A | Chemical drug | 1.79E−4 | Activated |
| | | | | MYCN | Transcription regulator | 1.40E−3 | Suppressed |
| | | | | Butyric acid | Chemical-endogenous | 3.59E−3 | Activated |
| | | | | ERK1/2 | Group | 3.65E−3 | Activated |
| | | | | Romidepsin | Biologic drug | 1.82E−2 | Activated |
| | | | | HDAC1 | Transcription regulator | 4.02E−2 | Suppressed |
| | | | | HDAC2 | Transcription regulator | 4.32E−2 | Suppressed |

Figure 9:
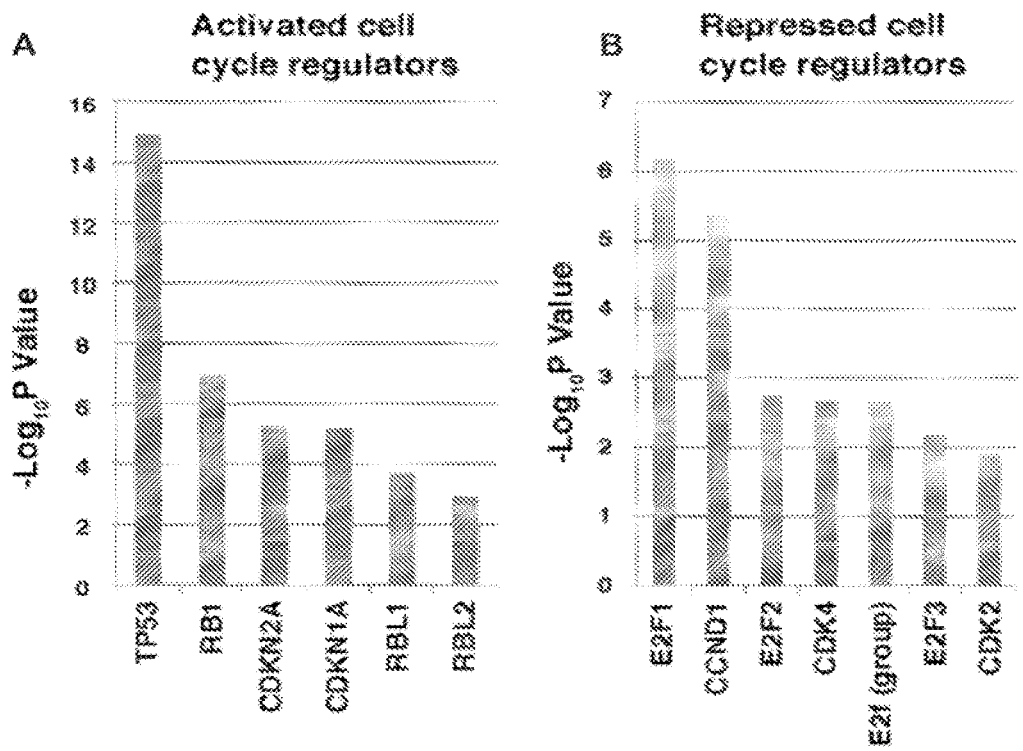
FIG. 9. depicts the cell cycle regulation genes in MDA-MB-231 cells that were (A) activated (e.g., TP53, RB1, CDKN2A, CDKN1A, RBL1, and RBL2) and (B) repressed (e.g., E2F1, CCND1, E2F2, CDK4, E2f group, E2F3, and CDK2) upon exposure to UF010 at 1 µM for 24 hours based on the Ingenuity Upstream Regulator analysis. The P-value is shown in negative Log 10 scale.
Figure 10:
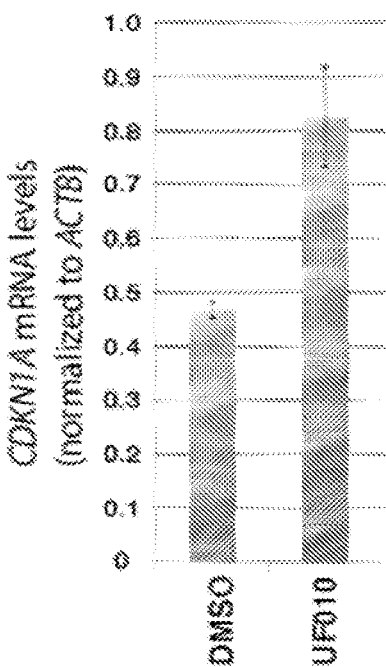
FIG. 10. depicts the qPCR validation of UF010-induced upregulation of CDKNIA encoding p 21. Shown are the average values of three experiments SEM.

As discussed above, UF010 induces G1 cell cycle arrest in FACS analysis (FIG. 6). Concordantly, pathway analysis of our gene expression data also revealed that UF010 activated pathways that promote G1 arrest, while suppressing mechanisms that promote cell cycle progression (FIGS. 9(A)-(B)). UF010-induced activation of CDKNA encoding p21 was also confirmed by quantitative real-time PCR (FIG. 10). As expected of an HDACi, this analysis also revealed that UF010 activated overlapping downstream effectors of the known HDACi, including tributyrin, butyric acid, trichostatin A (TSA), and romidepsin (Table 4). The inhibition of both HDAC 1 and HDAC 2 was also revealed in the pathway analysis (Table 4), thereby providing an independent validation of UF010 as a class I-specific HDACi. Interestingly, UF010 also seems to show overlapping functions with several other drugs, especially genotoxic chemotherapeutics, including cisplatin, camptothecin, doxorubicin and etoposide (Table 4 and data not shown). This is consistent with the ability of UF010 and other HDACi to elicit DNA-damage response [Lee, J. H., Choy, M. L., Ngo, L., Foster, S. S., and Marks, P. A. (2010). Histone deacetylase inhibitor induces DNA damage, which normal but not transformed cells can repair. Proceedings of the National Academy of Sciences of the United States of America 107, 14639-14644].

Example 52: In Vivo Assessment of UF010

Figure 12:
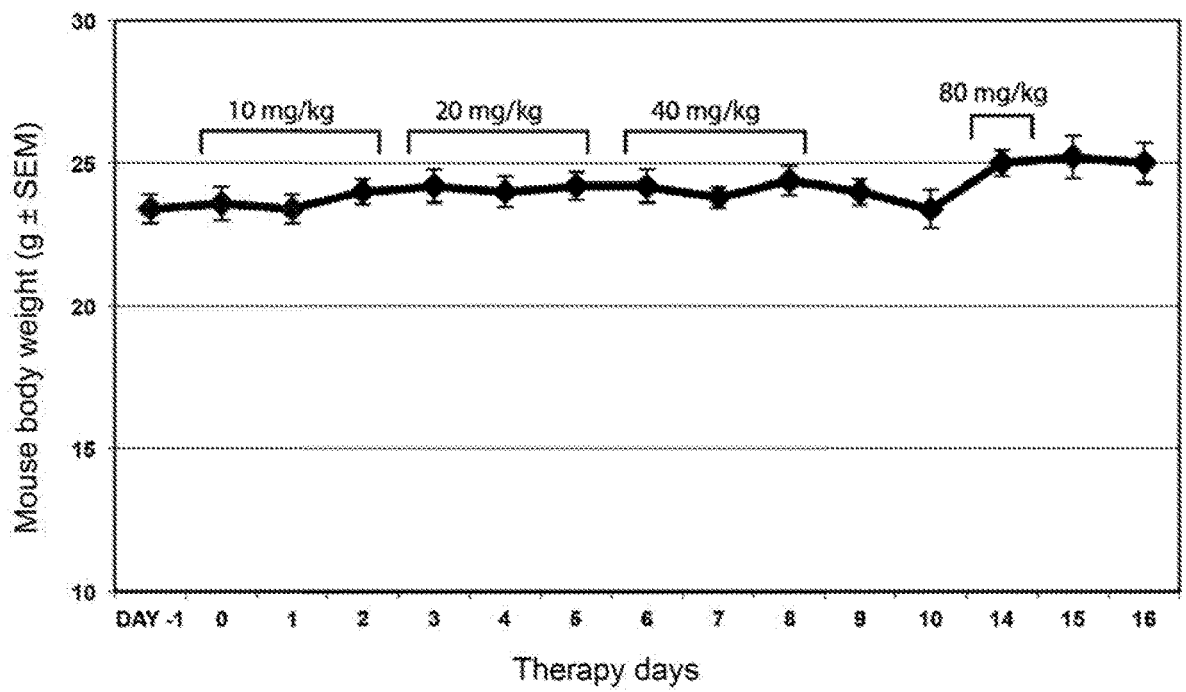
FIG. 12 illustrates the doses of UF010 for therapy days and mouse body weight.

Mice were orally dosed once daily with UF010 at the doses indicated in FIG. 12 by completely dissolving UF010 in 20% 2-hydroxypropyl-o-cyclodextrin at 1 mg/ml. The body weights were assessed once daily. No signs of abnormal physical or mental behaviors were observed during the experimental period. Shown are average body weights along with standard error of the mean (SEM, n=5). Oral dosing of UF010 at 80 mg/kg was completely tolerated without any signs of toxicity or loss of body weight, indicating its maximal tolerated dose (MTD) is >80 mg/kg. Similar to humans, entinostat is also poorly tolerated by animals. The MTD of entinostat is 3.1 mg/kg in rat, which is roughly equivalent to 1.5 mg/kg in mouse. Thus, the UF010 MTD is at least 50-fold higher than that of entinostat.

Head-to-head comparison also shows that UF010 exhibits better plasma drug exposure (AUC) and maximum plasma drug concentration ($C_{max}$) than another aminobenzamide analog 4b [Beconi M, Aziz O, Matthews K, Moumne L, O'Connell C, Yates D, Clifton S, Pett H, Vann J, Crowley L, Haughan A F, Smith D L, Woodman B, Bates G P, Brookfield F, Burli R W, McAllister G, Dominguez C, Munoz-Sanjuan I, Beaumont V. Oral administration of the pimelic diphenylamide HDAC inhibitor HDACi 4b is unsuitable for chronic inhibition of HDAC activity in the CNS in vivo. PLoS One. 2012; 7:e44498.] (shown below). The high tolerability of UF010 indicates that desirable therapeutic efficacy can be achieved by higher dosages and more frequent dosing, which would not be possible for entinostat due poor tolerability.

Pharmacologically, UF010 is more potent in inhibiting HDACs 2 and 3 than entinostat in vitro and, consistently, UF010 is about 5-fold more potent than entinostat in cell-based assays [Wang Y, Stowe R L, Pinello C E, Tian G, Madoux F, Li D, Zhao L Y, Li J L, Wang Y, Wang Y, H. M, Hodder P, Roush W R, Liao D. Identification of a Benzoylhydrazide Class of HDAC Inhibitors that Selectively Inhibit Class I HDACs. Chem Biol. 2015: in press.].

TABLE 5

In vivo drug properties of UF010 and entinostat

| PK parameter [a] | UF010 | Aminobenzamide analogs | |
| --- | --- | --- | --- |
| | | 4b [c] | Entinostat [d] |
| AUC nM hr | 6070 | 1080 | NA |
| $C_{max}$ nM | 5952 | 1130 | NA |
| $T_{max}$ hr | 0.25 | 0.25 | 0.5 |
| $T_{1/2}$ hr | 1.24 | 2.76 | ~1 |
| MTD [b] mg/kg | >80 | NA | 3.1 |

[a] UF010 (80 mg/kg) and 4b (50 mg/kg) were dosed orally.
[b] MTD was determined in mouse (UF010) or rat (entinostat).
[c] ref (4).
[d] ref (6).
NA: not available

Example 53: Cancer Cell Viability

Figure 11:
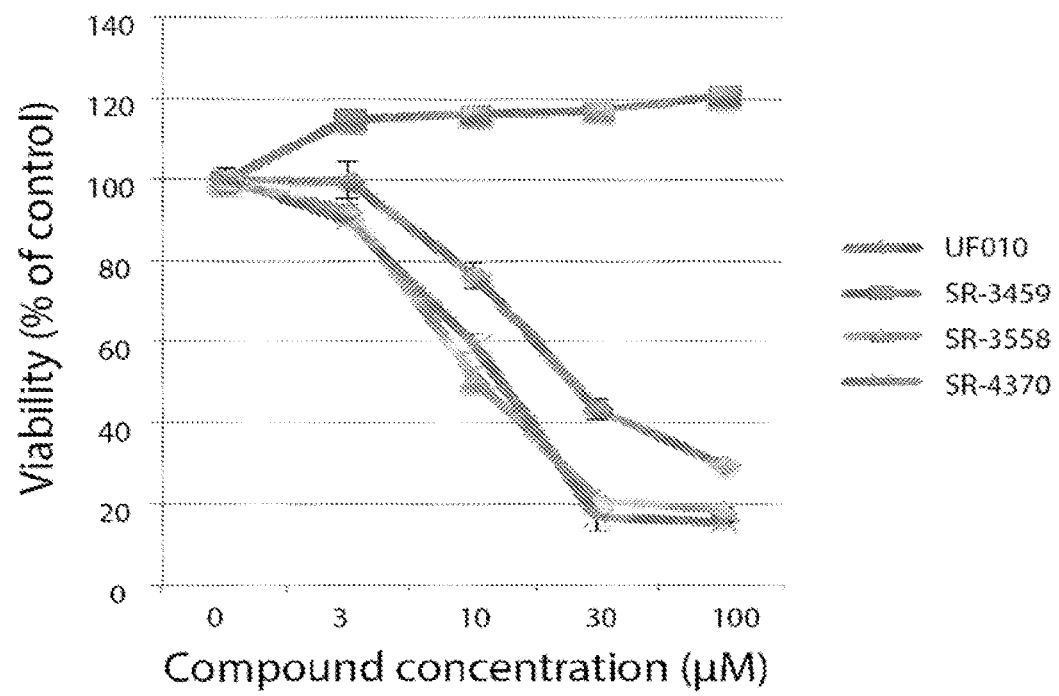
FIG. 11 depicts ability of the UF010 and analogs (benzoylhydrazides) on cancer cell viability and to induce cell death of the aggressive breast cancer MDA-MB-231 cells.

Compounds were examined for their HDAC inhibitory activity and their effect on cancer cell viability (MDA-MB-231 cells). The compounds' HDAC-1, -2, and -3 inhibition potency was measured essentially as described herein (luminescence readout in place of fluorescence readout). As can be seen in the following Table 6, data provided below show that the ability of the UF010 analogs (benzoylhydrazides) to kill cancer cells strictly depends on their inhibition potency against class I HDACs. More potent HDAC inhibitors are more effective to induce cell death of the aggressive breast cancer MDA-MB-231 cells, while a structurally similar analog devoid of the activity to inhibit HDAC (SR-3459) does not impair cancer cell viability. FIG. 11 illustrates the effect of concentration of UF010, SR-3459, SR-3558, and SR-34370 on MDA-MB-231 cell viability.

TABLE 6

| Compound | Structure | HDAC inhibition potency ($IC_{50}$, μM) | | | Cancer Cell (MDA-MB-231) killing $IC_{50}$ (μM) |
| --- | --- | --- | --- | --- | --- |
| | | HDAC1 | HDAC2 | HDAC3 | |
| UF010 | (4-bromophenyl)-C(=O)-NH-NH-butyl | 0.46 | 1.33 | 0.19 | 31 |

TABLE 6-continued

| Compound | Structure | HDAC inhibition potency (IC$_{50}$, μM) | | | Cancer Cell (MDA-MB-231) killing |
|---|---|---|---|---|---|
| | | HDAC1 | HDAC2 | HDAC3 | IC$_{50}$ (μM) |
| SR-3459 | | No inhibition | No inhibition | No inhibition | >100 |
| SR-3558 | | 0.09 | 0.8 | 0.06 | 12.3 |
| SR-4370 | | 0.13 | 0.58 | 0.006 | 12.6 |

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed is:

1. A compound according to Formula I or a salt thereof:

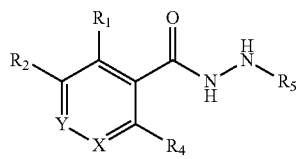

(I)

wherein:
X is CH;
Y is C—R$_3$;
R$_1$, R$_2$, and R$_4$ are H;
R$_3$ is a substituted or unsubstituted aryl group or a substituted or unsubstituted heteroaryl group, wherein the substituted heteroaryl group or the substituted aryl group is substituted with one or more substituents selected from alkyl, alkenyl, alkynyl, cycloalkyl, aralkyl, heteroaralkyl, aryl, heteroaryl, halogen, haloalkyl, cyano, alkoxy, aryloxy, hydroxyl, hydroxylalkyl, carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, arylsulfonyl, alkylaminocarbonyl, alkylcarbonyl, aralkylaminocarbonyl, amido, alkylaminosulfonyl, arylaminosulfonyl, dialkylaminosulfonyl, alkylsulfonylamino, arylsulfonylamino, carbamido, carbamyl, thioureido, thiocyanato, sulfoamido, sulfonylalkyl, or sulfonylaryl; and
R$_5$ is branched or straight chain C$_{1-12}$ alkyl optionally substituted with a cycloalkyl group.

2. The compound of claim 1, wherein R$_3$ is an unsubstituted phenyl group.

3. The compound of claim 1, wherein R$_3$ is a phenyl group substituted with one or more halogen atoms, alkyl groups, or a combination thereof.

4. The compound of claim 1, wherein R$_3$ is a phenyl group substituted with one or more fluoride atoms.

5. The compound of claim 1, wherein R$_3$ has the structure

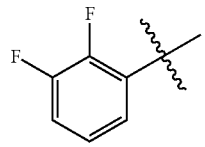

6. The compound of claim 1, wherein R$_3$ is a substituted or unsubstituted pyridyl, furanyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, isoquinolinyl, or indazolyl.

7. The compound of claim 1, wherein R$_3$ is a substituted or unsubstituted pyrimidinyl group.

8. The compound of claim 1, wherein $R_5$ is straight chain $C_{1-12}$ alkyl group substituted with a $C_{3-8}$ cycloalkyl group.

9. The compound of claim 1, wherein the compound has the structure

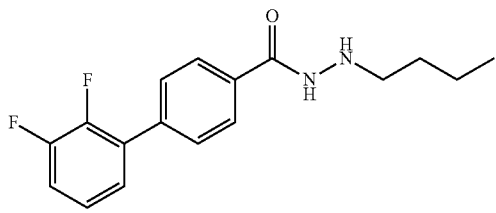

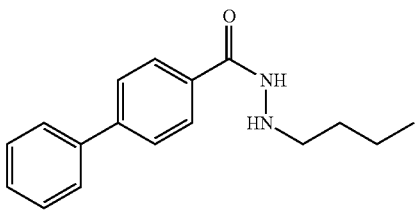 [SMILES: CCCCNNC(=O)c1ccc(-c2ccccc2)cc1]

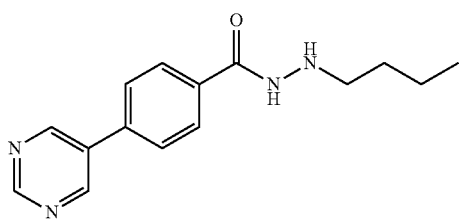

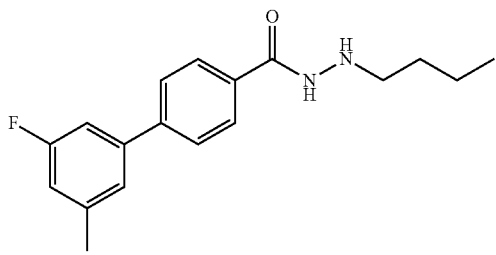

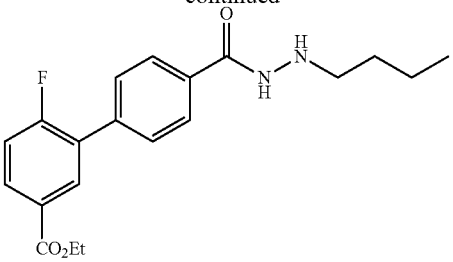

or a salt thereof.

10. The compound of claim 1, wherein the compound has the structure

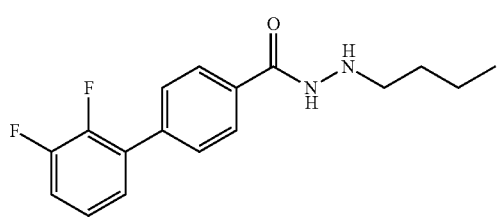

or a salt thereof.

11. A pharmaceutical composition comprising the compound of claim 1 or a salt thereof and a pharmaceutically acceptable carrier.

12. A method of treating cancer in a subject, comprising administering to said subject in need thereof, an effective amount of a compound of claim 1 or the salt thereof, wherein the cancer is selected from the group consisting of breast cancer, liver cancer, colon cancer, leukemia, non-small cell lung cancer, central nervous system cancer, melanoma, ovarian cancer, renal cancer, and prostate cancer.

13. The method of claim 12, wherein the cancer is breast cancer.

14. A method of treating a subject suffering from or susceptible to a cell proliferation related disorder or disease, wherein the subject has been identified as in need of treatment for a cell proliferation related disorder or disease, comprising administering to said subject in need thereof, an effective amount of a compound of claim 1 or the salt thereof, wherein the cell proliferation related disorder or disease is selected from the group consisting of breast cancer, liver cancer, colon cancer, leukemia, non-small cell lung cancer, central nervous system cancer, melanoma, ovarian cancer, renal cancer, and prostate cancer.

* * * * *